United States Patent
Laurent et al.

(10) Patent No.: US 6,602,303 B2
(45) Date of Patent: Aug. 5, 2003

(54) COMPOSITION FOR THE OXIDATION DYEING OF KERATINOUS FIBERS COMPRISING AT LEAST ONE OXIDATION DYE AND AT LEAST ONE CATIONIC AMPHIPHILIC POLYMER, AND DYEING METHODS

(75) Inventors: Florence Laurent, Asnieres (FR); Delphine Allard, Colombes (FR)

(73) Assignee: L'Oreal S.A., Paris (FR)

( * ) Notice: Subject to any disclaimer, the term of this patent is extended or adjusted under 35 U.S.C. 154(b) by 159 days.

(21) Appl. No.: 09/927,510

(22) Filed: Aug. 13, 2001

(65) Prior Publication Data

US 2003/0000026 A9 Jan. 2, 2003

(30) Foreign Application Priority Data

Aug. 11, 2000 (FR) .............................. 00 10593

(51) Int. Cl.$^7$ ................................ A61K 7/13
(52) U.S. Cl. ................ 8/405; 8/406; 8/407; 8/408; 8/409; 8/410; 8/412; 8/421; 8/425; 8/554
(58) Field of Search ................ 8/405, 406, 407, 8/408, 409, 410, 412, 425, 554

(56) References Cited

U.S. PATENT DOCUMENTS

| | | | |
|---|---|---|---|
| 2,261,002 A | 10/1941 | Ritter | 260/570 |
| 2,271,378 A | 1/1942 | Searle | 167/22 |
| 2,273,780 A | 2/1942 | Dittmar | 260/28 |
| 2,375,853 A | 5/1945 | Kirby et al. | 260/583 |
| 2,388,614 A | 11/1945 | Kirby et al. | 167/22 |
| 2,454,547 A | 11/1948 | Bock et al. | 260/567.6 |
| 2,961,347 A | 11/1960 | Floyd | 117/141 |
| 3,206,462 A | 9/1965 | McCarty | 260/256.4 |
| 3,227,615 A | 1/1966 | Korden | 167/87.1 |
| 3,632,559 A | 1/1972 | Matter et al. | 260/78 |
| 3,836,537 A | 9/1974 | Boerwinkle et al. | 260/29.6 |

(List continued on next page.)

FOREIGN PATENT DOCUMENTS

| | | |
|---|---|---|
| DE | 23 59 399 | 6/1975 |
| DE | 38 43 892 | 6/1990 |
| DE | 41 33 957 | 4/1993 |
| DE | 195 43 988 | 5/1997 |
| EP | 0 080 976 | 6/1983 |
| EP | 0 122 324 | 10/1984 |
| EP | 0 824 914 | 2/1988 |
| EP | 0 825 200 | 2/1988 |
| EP | 0 337 354 | 10/1989 |
| EP | 0 673 641 | 9/1995 |
| EP | 0 943 320 | 9/1999 |
| EP | 1 090 623 | 4/2001 |
| FR | 1 400 366 | 12/1965 |
| FR | 1 492 597 | 8/1967 |
| FR | 1 583 363 | 10/1969 |
| FR | 2 077 143 | 10/1971 |
| FR | 2 080 759 | 11/1971 |
| FR | 2 162 025 | 7/1973 |
| FR | 2 190 406 | 2/1974 |
| FR | 2 252 840 | 6/1975 |
| FR | 2 270 846 | 12/1975 |
| FR | 2 280 361 | 2/1976 |
| FR | 2 316 271 | 1/1977 |
| FR | 2 320 330 | 3/1977 |
| FR | 2 336 434 | 7/1977 |
| FR | 2 368 508 | 5/1978 |
| FR | 2 383 660 | 10/1978 |
| FR | 2 393 573 | 1/1979 |
| FR | 2 413 907 | 8/1979 |
| FR | 2 470 596 | 6/1981 |
| FR | 2 505 348 | 11/1982 |
| FR | 2 519 863 | 7/1983 |
| FR | 2 542 997 | 9/1984 |
| FR | 2 598 611 | 11/1987 |
| FR | 2 733 749 | 11/1996 |
| JP | 2-19576 | 1/1990 |
| JP | 9-110659 | 4/1997 |
| WO | WO 94/08969 | 4/1994 |
| WO | WO 94/08970 | 4/1994 |
| WO | WO 96/15765 | 5/1996 |
| WO | WO 00/68282 | 11/2000 |

OTHER PUBLICATIONS

English language Derwent Abstract of EP 0 080 976, Jul. 8, 1983.
English language Derwent Abstract of EP 0 943 320, Sep. 22, 1999.
English language Derwent Abstract of EP 1 090 623, Apr. 11, 2001.
English language Derwent Abstract of FR 2 077 143, Oct. 15, 1971.
English language Derwent Abstract of FR 2 080 759, Nov. 19, 1971.
English language Derwent Abstract of FR 2 320 330, Mar. 4, 1977.
English language Derwent Abstract of FR 2 336 434, Jul. 22, 1977.
English language Derwent Abstract of JP 2–19576 Jan. 23, 1990.
English language Derwent Abstract of JP 9–110659, Apr. 28, 1997.

Primary Examiner—Charles Boyer
Assistant Examiner—Eisa B Elhilo
(74) Attorney, Agent, or Firm—Finnegan, Henderson, Farabow, Garrett & Dunner, L.L.P.

(57) ABSTRACT

Compositions for oxidation dyeing of keratinous fibers, for example, human keratinous fibers such as hair, further such as human hair, comprising, in a medium suitable for dyeing, at least one oxidation dye, at least one cationic amphiphilic polymer comprising at least one fatty chain, and a combination comprising: (I) at least one compound chosen from oxyalkylenated and glycerolated fatty alcohols and (II) at least one hydroxylated solvent, wherein the hydroxylated solvent may have a molecular weight of less than 250, and wherein the weight ratio of (I) to (II) is greater than 1:1 and dyeing processes and devices, such as kits, comprising such compositions.

98 Claims, No Drawings

U.S. PATENT DOCUMENTS

| | | | |
|---|---|---|---|
| 3,917,817 A | 11/1975 | Vanlerberghe et al. | 424/70 |
| 3,929,990 A | 12/1975 | Green et al. | 424/78 |
| 3,966,904 A | 6/1976 | Green et al. | 424/78 |
| 4,001,432 A | 1/1977 | Green et al. | 424/329 |
| 4,003,699 A | 1/1977 | Rose et al. | 8/10.2 |
| 4,005,193 A | 1/1977 | Green et al. | 424/168 |
| 4,013,787 A | 3/1977 | Varlerberghe et al. | 424/70 |
| 4,025,617 A | 5/1977 | Green et al. | 424/78 |
| 4,025,627 A | 5/1977 | Green et al. | 424/248.4 |
| 4,025,653 A | 5/1977 | Green et al. | 424/325 |
| 4,026,945 A | 5/1977 | Green et al. | 260/567.6 |
| 4,027,008 A | 5/1977 | Sokol | 424/62 |
| 4,027,020 A | 5/1977 | Green et al. | 424/248.56 |
| 4,031,307 A | 6/1977 | DeMartino et al. | 536/114 |
| 4,131,576 A | 12/1978 | Iovine et al. | 260/17.4 |
| 4,157,388 A | 6/1979 | Christiansen | 424/70 |
| 4,172,887 A | 10/1979 | Vanlerberghe et al. | 424/70 |
| 4,223,009 A | 9/1980 | Chakrabarti | 424/47 |
| 4,277,581 A | 7/1981 | Vanlerberghe et al. | 525/420 |
| 4,349,532 A | 9/1982 | Vanlerberghe et al. | 424/47 |
| 4,591,610 A | 5/1986 | Grollier | 524/55 |
| 4,608,250 A | 8/1986 | Jacquet et al. | 424/71 |
| 4,702,906 A | 10/1987 | Jacquet et al. | 424/70 |
| 4,719,099 A | 1/1988 | Grollier et al. | 424/47 |
| 4,719,282 A | 1/1988 | Nadolsky et al. | 528/310 |
| 4,761,273 A | 8/1988 | Grollier et al. | 424/47 |
| 4,839,166 A | 6/1989 | Grollier et al. | 424/71 |
| 4,996,059 A | 2/1991 | Grollier et al. | 424/71 |
| 5,061,289 A | 10/1991 | Clausen et al. | 8/405 |
| 5,139,037 A | 8/1992 | Grollier et al. | 132/203 |
| 5,196,189 A | 3/1993 | Jacquet et al. | 424/72 |
| 5,380,340 A | 1/1995 | Neunhoeffer et al. | 8/409 |
| 5,735,908 A | 4/1998 | Cotteret et al. | 8/410 |
| 5,766,576 A | 6/1998 | Lowe et al. | 424/62 |
| 5,976,195 A * | 11/1999 | de la Mettrie et al. | 8/411 |
| 6,099,592 A | 8/2000 | Vidal et al. | 8/409 |

* cited by examiner

COMPOSITION FOR THE OXIDATION DYEING OF KERATINOUS FIBERS COMPRISING AT LEAST ONE OXIDATION DYE AND AT LEAST ONE CATIONIC AMPHIPHILIC POLYMER, AND DYEING METHODS

The present invention relates to a composition for the oxidation dyeing of keratinous fibers, such as human keratinous fibers for example hair, comprising, in a medium suitable for dyeing:
(a) at least one oxidation dye,
(b) at least one cationic amphiphilic polymer comprising at least one fatty chain, and
(c) a combination comprising:
  (I) at least one compound chosen from oxyalkylenated fatty alcohols and glycerolated fatty alcohols, and
  (II) at least one hydroxylated solvent,
  wherein the weight ratio of (I) to (II) is greater than 1:1.

It is known to dye keratinous fibers, such as human hair, with dyeing compositions comprising oxidation dyes, such as, oxidation dye precursors (for example, ortho-phenylenediamines, para-phenylenediamines, ortho-aminophenols, para-aminophenols, and heterocyclic bases generally called oxidation bases).

The oxidation dye precursors, or oxidation bases, are colorless or weakly colored compounds. When these compounds are combined with oxidizing products, dyes and colored compounds may form by a process of oxidative condensation of the oxidation bases.

It is also known that the shades obtained with these oxidation bases can be varied by combining them with couplers or color modifiers, the latter may be chosen from aromatic meta-diamines, meta-aminophenols, meta-diphenols and certain heterocyclic compounds.

The variety of molecules used in oxidation dyes (oxidation bases and couplers), allows a rich palette of colors to be obtained.

Upon application of the oxidation dye product to hair, it is desirable to localize the oxidation dye product correctly so that the dye product does not run down the face or outside of the areas intended to be dyed. It is also desirable to obtain a uniform and even coloration over the entire head of hair.

It is also desirable for the compositions containing oxidation dyes to be stable over time such as for example, rheologically stable, before the oxidation dye composition is mixed with an oxidizing agent.

European patent application No. 0 943 320 discloses formulations for oxidation dye products which include cationic associative polymers chosen from quaternized celluloses and hydroxyethylcelluloses comprising at least one fatty chain in order to obtain the above-mentioned properties.

In addition to at least one of the good qualities offered by the dye compositions disclosed in European patent application No. 0 943 320, the dye composition may also exhibit at least one of the following properties: intense and chromatic (luminous) colorations, low selectivity, exhibit good fastness (resistance) towards external agents, for example, chemical agents (shampoo, and permanent-waving products) and natural agents (light, perspiration) giving hair good cosmetic properties.

Nevertheless, the inventors have found that the color obtained by combining the oxidation dye composition and the oxidizing agent composition may develop too quickly. For example, the color may darken very quickly during the time that the mixture is left on the hair, which may indicate a premature oxidation of the dyes, resulting in a disruption of the dyeing and the development of an aesthetic problem.

However, after considerable research, the inventors have discovered that the addition of a combination of materials, as described below, into a composition that combines an oxidation dyeing composition and at least one oxidizing agent, develops in color much less quickly, thus reducing the premature oxidation of the oxidation dyes. This discovery forms one aspect of the present invention.

One embodiment of the present invention is a composition for the oxidation dyeing of keratinous fibers, for example human keratinous fibers such as hair, comprising, in a medium suitable for dyeing:
(a) at least one oxidation dye,
(b) at least one cationic amphiphilic polymer comprising at least one fatty chain, and
(c) a combination comprising:
  (I) at least one compound chosen from oxyalkylenated fatty alcohols and glycerolated fatty alcohols, and
  (II) at least one hydroxylated solvent having a molecular weight of less than 250,
  wherein the weight ratio of (I) to (II) is greater than 1:1.

Another embodiment of the invention relates to a ready-to-use composition for the oxidation dyeing of keratinous fibers, for example human keratinous fibers such as hair, comprising, in a medium suitable for dyeing:
(a) at least one oxidation dye,
(b) at least one cationic amphiphilic polymer comprising at least one fatty chain, and
(c) a combination comprising:
  (I) at least one compound chosen from oxyalkylenated fatty alcohols and glycerolated fatty alcohols, and
  (II) at least one hydroxylated solvent having a molecular weight of less than 250,
  wherein the weight ratio of (I) to (II) is greater than 1:1; and
(d) at least one oxidizing agent.

For the purposes of the invention, the expression "ready-to-use composition" is understood to mean any composition intended to be applied immediately to the keratinous fibers; either applied as stored before use or obtained from combining two or more compositions and applied.

Another embodiment of the invention is a process for dyeing keratinous fibers, for example, keratinous fibers such as hair, comprising:
(1) storing a composition (A) comprising, in a medium suitable for dyeing:
  (a) at least one oxidation dye,
  (b) at least one cationic amphiphilic polymer comprising at least one fatty chain, and
  (c) a combination comprising:
    (I) at least one compound chosen from oxyalkylenated fatty alcohols and glycerolated fatty alcohols, and
    (II) at least one hydroxylated solvent having a molecular weight of less than 250,
    wherein the weight ratio of (I) to (II) is greater than 1:1;
(2) storing, separately from said composition (A), a composition (B) comprising, in a medium suitable for dyeing, at least one oxidizing agent;
(3) applying said composition (A) and said composition (B) to keratinous fibers, and
(4) developing a color on keratinous fibers, such as hair; wherein said composition (A) is combined at the time of use with said composition (B) and applied to keratinous fibers, such as hair, or wherein said composition (A) and said composition (B) are applied sequentially to said keratinous fibers, such as hair, without intermediate rinsing.

Another embodiment of the invention is a device or "kit" for the oxidation dyeing of keratinous fibers, for example, human keratinous fibers such as hair, comprising at least two compartments, wherein:

(1) a first compartment comprises, in a medium suitable for dyeing:
  (a) at least one oxidation dye,
  (b) at least one cationic amphiphilic polymer comprising at least one fatty chain, and
  (c) a combination comprising:
    (I) at least one compound chosen from oxyalkylenated fatty alcohols and glycerolated fatty alcohols, and
    (II) at least one hydroxylated solvent having a molecular weight of less than 250,
  wherein the weight ratio of (I) to (II) is greater than 1:1; and (2) a second compartment comprises, in a medium suitable for dyeing, at least one oxidizing agent.

At Least One Cationic Amphiphilic Polymer

The chemical structure of the amphiphilic polymers may comprise at least one hydrophilic zone providing the solubility in water, and at least one hydrophobic zone by which the polymers, in an aqueous medium, assemble with each other or with the hydrophobic portions of other molecules. The amphiphilic polymers are also termed "associative polymers", that is to say water-soluble polymers which are capable in an aqueous medium, of reversibly "associating" with each other or with other molecules.

According to the invention, the at least one cationic amphiphilic polymer comprising at least one fatty chain may be chosen for example from quaternized cellulose derivatives, cationic polyurethanes, cationic polyvinyllactams and acrylic terpolymers.

A. Quaternized Cellulose Derivatives

Non-limiting examples of quaternized cellulose derivatives may be chosen, for example, from:

quaternized celluloses modified with at least one group comprising at least one fatty chain, wherein said at least one group is chosen for example, from alkyl groups, arylalkyl groups, and alkylaryl groups and contains at least 8 carbon atoms; and quaternized hydroxyethylcelluloses modified with at least one group comprising at least one fatty chain, wherein said at least one group is chosen for example, from alkyl groups, arylalkyl groups, and alkylaryl groups and contains at least 8 carbon atoms.

In specific embodiments of the invention, the alkyl groups borne by the quaternized celluloses and hydroxyethylcelluloses may for example comprise from 8 to 30 carbon atoms. The aryl groups for example, may be chosen from phenyl groups, benzyl groups, naphthyl groups, and anthryl groups.

Non-limiting examples of quaternized alkylhydroxyethylcelluloses containing $C_8$–$C_{30}$ fatty chains may be chosen from the products QUATRISOFT LM 200, QUATRISOFT LM-X 529-18-A, QUATRISOFT LM-X 529-18B ($C_{12}$ alkyl) and QUATRISOFT LM-X 529-8 ($C_{18}$ alkyl) sold by the company Amerchol, and the products CRODACEL QM, Crodacel QL ($C_{12}$ alkyl) and Crodacel QS ($C_{18}$ alkyl) sold by the company Croda.

B. Cationic Polyurethanes

An example of a family of cationic amphiphilic polyurethanes which may be utilized in accordance with the invention is described in French patent application No. 0 009 609, incorporated by reference, herein. These polyurethanes may be chosen from the cationic amphiphilic polyurethanes of formula (Ia):

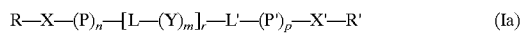

R—X—(P)$_n$—[L—(Y)$_m$]$_r$—L'—(P')$_p$—X'—R'     (Ia)

wherein:

R and R', which may be identical or different, are each chosen from hydrophobic groups and hydrogen atoms;

X and X', which may be identical or different, are each chosen from groups comprising an amine function optionally comprising a hydrophobic group, and a group L";

L, L", and L' which may be identical or different, are each chosen from derivatives of diisocyanates;

P and P', which may be identical or different, are each chosen from groups comprising an amine function optionally bearing at least one hydrophobic group;

Y is chosen from hydrophilic groups;

r is an integer from 1 to 100, such as from 1 to 50 and further for example, from 1 to 25;

n, m and p which may be identical or different, are chosen from numbers ranging from 0 to 1000;

provided that said cationic amphiphilic polyurethanes comprise at least one group chosen from protonated amine functions and quaternized amine functions, and at least one group chosen from hydrophobic groups.

In one embodiment of the invention, the only hydrophobic groups in the cationic amphiphilic polyurethanes are the groups R and R' at the ends of the chain.

In another example, the family of cationic amphiphilic polyurethanes may be chosen from the cationic amphiphilic polyurethanes of formula (Ia):

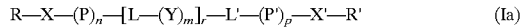

R—X—(P)$_n$—[L—(Y)$_m$]$_r$—L'—(P')$_p$—X'—R'     (Ia)

wherein:

R and R' which may be identical or different, are each chosen from hydrophobic groups, X and X' which may be identical or different, are each chosen from a group L", n and p which may be identical or different, are each chosen from numbers ranging from 1 to 1000;

L, L", and L' which may be identical or different, are each chosen from derivatives of diisocyanates;

P and P', which may be identical or different, are each chosen from groups comprising an amine function optionally bearing at least one hydrophobic group;

Y is chosen from hydrophilic groups;

r is an integer from 1 to 100, such as from 1 to 50 and further for example, from 1 to 25; and m is a number ranging from 0 to 1000.

In yet another example another embodiment the family of cationic amphiphilic polyurethanes is chosen from the cationic amphiphilic polyurethanes of formula (Ia):

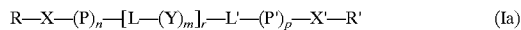

R—X—(P)$_n$—[L—(Y)$_m$]$_r$—L'—(P')$_p$—X'—R'     (Ia)

wherein:

R and R' which may be identical or different, are each chosen from hydrophobic groups, X and X' which may be identical or different are each chosen from a group L", n and p are each equal to 0, L, L", and L' which may be identical or different, are each chosen from derivatives of diisocyanates;

P and P', which may be identical or different, are each chosen from groups comprising an amine function optionally bearing at least one hydrophobic group;

Y is chosen from hydrophilic groups;

r is an integer from 1 to 100, such as from 1 to 50 and further for example, from 1 to 25; and m is a number ranging from 0 to 1000.

In this particular embodiment, the fact that n and p are equal to 0 means that these polymers comprise no units derived from a monomer containing an amine function incorporated into the polymer during the polycondensation. The protonated amine functions of these polyurethanes result from the hydrolysis of excess isocyanate functions at the end of the chain, followed by alkylation of the primary amine functions formed with alkylating agents containing a hydrophobic group. For example, these are compounds of the type RQ or R'Q, in which R and R' are as defined above and Q is chosen from leaving groups such as for example, halides, and sulfates.

In yet another embodiment, the family of cationic amphiphilic polyurethanes which may be utilized in accordance with the invention are those chosen from cationic amphiphilic polyurethanes of formula (Ia):

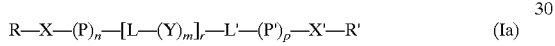

$$R-X-(P)_n-[L-(Y)_m]_r-L'-(P')_p-X'-R' \qquad (Ia)$$

wherein:

R and R' which may be identical or different, are each chosen from hydrophobic groups, X and X' which may be identical or different, are each chosen from groups comprising a quaternary amine, n and p are both equal to 0, L, and L' which may be identical or different, are each chosen from derivatives of diisocyanates;

P and P', which may be identical or different, are each chosen from groups comprising an amine function optionally bearing at least one hydrophobic group;

Y is chosen from hydrophilic groups;

r is an integer from 1 to 100, such as from 1 to 50 and further for example, from 1 to 25; and m is a number ranging from 0 to 1000;

The number-average molecular mass of the cationic amphiphilic polyurethanes may range, for example, from 400 to 500,000, such as from 1000 to 400,000, and further from 1000 to 300,000.

In one embodiment of the invention, the at least one cationic amphiphilic polyurethanes have at least one hydrophobic group comprising from 10 to 30 carbon atoms.

The term "hydrophobic groups" means groups and polymers chosen from optionally saturated, linear and branched, hydrocarbon-based chains, wherein said hydrocarbon-based chains may optionally comprise at least one hetero atom such as, P, O, N and S, and may optionally comprise at least one group chosen from perfluoro chains and silicone chains. In one embodiment of the invention, the hydrophobic groups are chosen from hydrocarbon-based groups, wherein said hydrophobic groups comprise at least 10 carbon atoms, such as for example, from 10 to 30 carbon atoms, further from 12 to 30 carbon atoms and further still from 18 to 30 carbon atoms.

In another embodiment of the invention, the hydrocarbon-based groups are derivatives of monofunctional compounds.

By way of example, the hydrophobic groups may be chosen from derivatives of fatty alcohols such as for example, stearyl alcohol, dodecyl alcohol and decyl alcohol. The hydrophobic groups also may be chosen from hydrocarbon-based polymers such as, for example, polybutadiene.

When at least one of X and X' is a group chosen from groups comprising tertiary amines and groups comprising quaternary amines, then at least one of X and X' may be chosen from amines of following formulae:

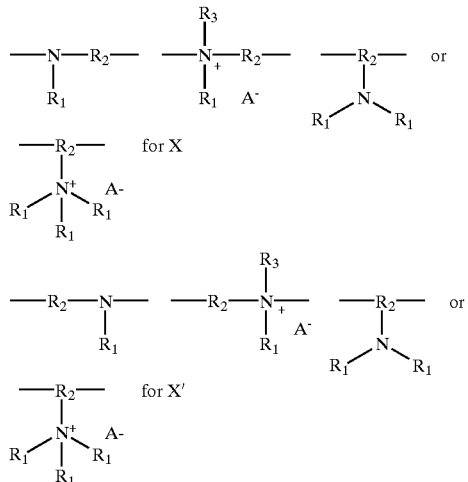

wherein:

$R_2$ which may be identical or different, are each chosen from linear and branched, alkylene groups containing from 1 to 20 carbon atoms, wherein said linear and branched alkylene groups optionally comprise a unit chosen from saturated rings and unsaturated rings, such as arylene groups, and further wherein at least one carbon atom is optionally replaced with a hetero atom chosen from N, S, O and P;

$R_1$ and $R_3$, which may be identical or different, are each chosen from linear and branched $(C_1-C_{30})$alkyl groups, linear and branched $(C_1-C_{30})$alkenyl and an aryl group, wherein at least one carbon atom is optionally replaced with a hetero atom chosen from N, S, O and P; and $A^-$ which may be identical or different, are each chosen from physiologically acceptable counterions.

The groups L, L', and L" may represent a group of formula:

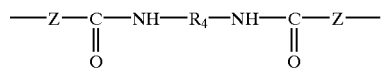

wherein:

Z is a group chosen from —O—, —S—, and —NH—; and $R_4$ is chosen from linear and branched, alkylene groups containing from 1 to 20 carbon atoms, wherein said linear and branched alkylene groups optionally comprise a unit chosen from saturated rings and unsaturated rings, such as arylene groups, and further wherein at least one carbon atom is optionally replaced with a hetero atom chosen from N, S, O and P.

The groups P and P' comprising an amine function may be chosen from groups of the following formulae:

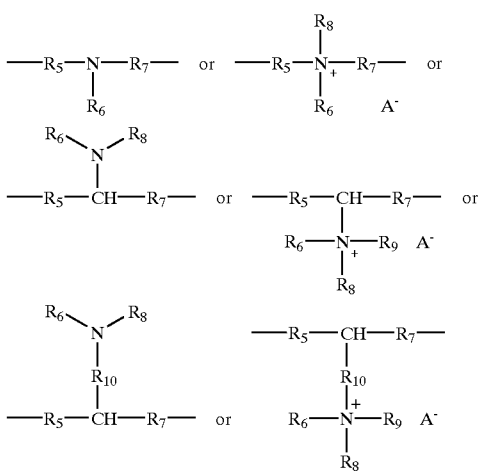

wherein:
- $R_5$ and $R_7$, which may be identical or different, are each chosen from linear and branched, alkylene groups containing from 1 to 20 carbon atoms, wherein said linear and branched alkylene groups optionally comprise a unit chosen from saturated rings and unsaturated rings, such as arylene groups, and further wherein at least one carbon atom is optionally replaced with a hetero atom chosen from N, S, O and P;
- $R_6$, $R_8$ and $R_9$, which may be identical or different, are each chosen from linear and branched $(C_1–C_{30})$alkyl groups, linear and branched $(C_1–C_{30})$alkenyl and an aryl group, wherein at least one carbon atom is optionally replaced with a hetero atom chosen from N, S, O and P;
- $R_{10}$, which may be identical or different, are each chosen from optionally unsaturated, linear and branched, alkylene groups, optionally comprising at least one hetero atom chosen from N, O, S and P, and
- $A^-$ which may be identical or different, are each chosen from physiologically acceptable counterions.

Regarding the meaning of Y, the term "hydrophilic groups" is understood to mean a polymeric water-soluble group or non-polymeric water-soluble group.

By way of example, when the hydrophilic groups are non-polymeric water-soluble groups, they may be chosen from ethylene glycol, diethylene glycol and propylene glycol.

When, in accordance with an embodiment of the invention, the hydrophilic groups are hydrophilic polymers, the hydrophilic polymers may comprise at least one polymer chosen, for example, from polyethers, sulfonated polyesters, sulfonated polyamides. Non-limiting examples of the hydrophilic groups may be chosen polyethers, poly(ethyleneoxides) and poly(propyleneoxides).

The cationic amphiphilic polyurethanes of formula (Ia) according to the invention may be formed from diisocyanates and from compounds with functions containing a labile hydrogen. Non-limiting examples of functions containing a labile hydrogen may be chosen from alcohols, primary amines, secondary amines, and thiols. These functions after reaction with the diisocyanate functions form polyurethanes, polyureas and polythioureas, respectively. The term "polyurethanes" in the present invention is understood to encompass these three types of polymer, namely polyurethanes, polyureas and polythioureas, as well as copolymers of these three types of polymers.

In accordance with the invention, a first type of compound involved in the preparation of the cationic amphiphilic polyurethanes of formula (Ia) comprises at least one unit containing an amine function. This compound may be chosen from multifunctional groups and difunctional groups. That is, a difuctional compound according to one embodiment, comprises two labile hydrogen atoms borne, for example, by a function chosen from hydroxyl functions, primary amine functions, secondary amine functions and thiol functions. In another embodiment, a mixture of multifunctional and difunctional compounds in which the percentage of multifunctional compounds is low may also be used.

As mentioned above, this compound may comprise more than one unit containing an amine function. In this case, it is may be a polymer bearing a repeating unit containing an amine function. Compounds of this type may for example, be chosen from the following formulae:

  (i)

  (ii)

wherein:
- Z is a group chosen from —O—, —S—, and —NH—;
- P and P', which may be identical or different, are each chosen from groups comprising an amine function optionally bearing at least one hydrophobic group; and
- n, and p which may be identical or different, are chosen from numbers ranging from 0 to 1000.

Representative examples of compounds containing an amine function may be chosen from N-methyldiethanolamine, N-tert-butyldiethanolamine and N-sulphoethyldiethanolamine.

In accordance with the invention, a second type of compound involved in the preparation of the cationic amphiphilic polyurethanes of formula (Ia) comprises diisocyanates corresponding to the formula:

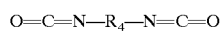

wherein $R_4$ is chosen from linear and branched, alkylene groups containing from 1 to 20 carbon atoms, wherein said linear and branched alkylene groups optionally comprise a unit chosen from saturated rings and unsaturated rings, such as arylene groups, further wherein at least one carbon atom is optionally replaced with a hetero atom chosen from N, S, O and P.

Representative examples of this second type of compound may be chosen, for example, from methylenediphenyl diisocyanate, methylenecyclohexane diisocyanate, isophorone diisocyanate, toluene diisocyanate, naphthalene diisocyanate, butane diisocyanate and hexane diisocyanate.

In accordance with the invention, a third type of compound involved in the preparation of the cationic amphiphilic polyurethanes of formula (Ia) comprises hydrophobic compounds intended to form the terminal hydrophobic groups of the polymer of formula (Ia).

This third type of compound comprises a hydrophobic group and a function containing a labile hydrogen chosen, for example, from hydroxyl functions, primary amine functions, secondary amine functions and thiol functions.

Non-limiting examples of the third type of compound may be chosen, for example, from fatty alcohols such as, stearyl alcohol, dodecyl alcohol and decyl alcohol. When this third type of compound comprises a polymeric chain, it may be chosen, for example, from α-hydroxylated hydrogenated polybutadienes.

According to the invention, the hydrophobic groups of the cationic amphiphilic polyurethanes of formula (Ia) may also result from the quaternization reaction of the tertiary amines of the compound comprising at least one tertiary amine unit. Thus, the hydrophobic groups are introduced via the quaternizing agent. This quaternizing agent is chosen, for example, from a compound of the following formulae:

$$RQ \quad (iii)$$

$$R'Q \quad (iv),$$

wherein:
- R and R' which may be identical or different, are each chosen from hydrophobic groups, and
- Q which may be identical or different, are each chosen from leaving groups such as halides and sulfates.

The cationic amphiphilic polyurethanes of formula (Ia) may also comprise at least one hydrophilic sequence. This at least one hydrophilic sequence is provided by a fourth type of compound involved in the preparation of the polymer. This fourth type of compound may comprise at least one function, that is, the compound may be, for example, multifunctional or difunctional. In one embodiment of the invention, the cationic amphiphilic polyurethanes of formula (Ia) comprise a mixture of multifunctional compounds and difunctional compounds, wherein the percentage of multifunctional compounds is low, such as lower than that of the difunctional compounds.

The functions containing a labile hydrogen are chosen, for example, from alcohol functions, primary amine functions, secondary amine functions and thiol functions. This compound may also be a polymer terminated at the chain ends with one of these functions containing a labile hydrogen.

By way of example, when the hydrophilic groups are non-polymeric water-soluble groups, they may be chosen from ethylene glycol, diethylene glycol and propylene glycol.

When, in accordance with an embodiment of the invention, the hydrophilic groups are hydrophilic polymers, the hydrophilic polymers may comprise at least one polymer chosen, for example, from polyethers, sulfonated polyesters, sulfonated polyamides. Non-limiting examples of the hydrophilic groups may be chosen polyethers, polyethyleneoxides and polypropyleneoxides.

The hydrophilic group termed Y in formula (Ia) is optional. Specifically, the units containing a quaternary or protonated amine function may suffice to provide the solubility or water-dispersibility required for this type of polymer in an aqueous solution. In one embodiment of the invention, the at least one cationic amphiphilic polyurethane comprises at least one hydrophilic group.

The at least one cationic amphiphilic polyurethane may be chosen from water-soluble polymers and water-dispersible polymers.

The term "water-soluble", for purposes of this invention, is understood to mean a compound with a solubility of more than 1% by weight in one liter of water at room temperature.

The term "water-dispersible", for purposes of this invention, is understood to mean a compound which spontaneously forms in water, globules with an average size ranging from 5 to 600 nm (measured by light scattering techniques with a Coulter apparatus).

Cationic Polyvinyllactams

The cationic poly(vinyllactam) polymers according to the invention may, for example, be formed from at least one monomer chosen from:
a) vinyllactam monomers and alkylvinyllactam monomers;
b) monomers chosen from formulae (Ib) and (IIb):

$$CH_2=C(R_1)-CO-X-(Y)_{\overline{p}}-(CH_2-CH_2-O)_{\overline{m}}-(CH_2-CH(R_2)-O)_{\overline{n}}-(Y_1)_{\overline{q}}-\overset{R_3+}{\underset{\underset{Z^-}{R_5}}{N}}-R_4 \quad (Ib)$$

$$CH_2=C(R_1)-CO-X-(Y)_{\overline{p}}-(CH_2-CH_2-O)_{\overline{m}}-(CH_2-CH(R_2)-O)_{\overline{n}}-(Y_1)_{\overline{q}}-N\overset{R_3}{\underset{R_4}{\diagdown}} \quad (IIb)$$

wherein:
- X which may be identical or different, are each chosen from oxygen and $NR_6$ groups,
- $R_1$ and $R_6$ which may be identical or different, are each chosen from hydrogen and linear and branched ($C_1$–$C_5$) alkyl groups,
- $R_2$ which may be identical or different, are each chosen from linear and branched ($C_1$–$C_4$)alkyl groups,
- $R_3$, $R_4$, and $R_5$ which may be identical or different, are each chosen from hydrogen, linear and branched ($C_1$–$C_{30}$)alkyl groups and groups chosen from formula (IIIb):

$$-(Y_2)_r-(CH_2-CH(R_7)-O)_x-R_8 \quad (IIIb)$$

wherein:
- Y, $Y_1$, and $Y_2$ which are identical or different, are each chosen from linear and branched ($C_2$–$C_{16}$)alkylene groups,
- $R_7$ is chosen from hydrogen, linear and branched ($C_1$–$C_4$) alkyl groups, and linear and branched ($C_1$–$C_4$) hydroxyalkyl groups,
- $R_8$ is chosen from hydrogen and linear and branched ($C_1$–$C_{30}$)alkyl groups,
- p, q, and r which are identical or different, are each a number chosen from 0 and 1,
- m and n which are identical or different, are each an integer ranging from 0 to 100,
- x is an integer ranging from 1 to 100,
- Z is an anion chosen from organic acid anions and inorganic acid anions, provided that:
  - at least one of $R_3$, $R_4$, $R_5$, and $R_8$ is chosen from linear and branched ($C_9$–$C_{30}$)alkyl groups,
  - if at least one of m and n is other than zero, then q is equal to 1,
  - if at least one of m and n are equal to zero, then at least one of p and q is equal to 0.

The cationic poly(vinyllactam) polymers according to the invention may be chosen from crosslinked polymers, non-crosslinked polymers and block polymers.

In one embodiment of the invention, the counterion, $Z^-$, of the monomers of formula (Ib), may be chosen from halide ions, phosphate ions, a methosulfate ion and a tosylate ion.

In another embodiment, $R_3$, $R_4$, and $R_5$ which are identical or different are each chosen from hydrogen and linear and branched ($C_1$–$C_{30}$)alkyl groups.

In another embodiment of the invention, the at least one monomer of formulae (Ib) and (IIb) is a monomer of formula (Ib) wherein m and n are equal to 0.

In yet another embodiment, the at least one monomer chosen from vinyllactam monomers and alkylvinyllactam monomers is a compound of formula (IVb):

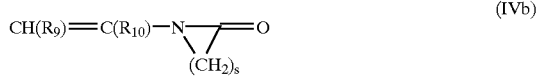

(IVb)

wherein:

s is an integer ranging from 3 to 6, $R_9$ is chosen from hydrogen and ($C_1$–$C_5$)alkyl groups, $R_{10}$ is chosen from hydrogen and ($C_1$–$C_5$)alkyl groups, with the proviso that at least one of $R_9$ and $R_{10}$ is hydrogen.

In one embodiment of the invention, the monomer (IVb) is vinylpyrrolidone.

The at least one cationic poly(vinyllactam) polymer according to the invention may further be formed from at least one additional monomer, chosen for example, from cationic monomers and nonionic monomers.

Representative compounds according to the invention, include the following terpolymers formed from:

a) one monomer of formula (IVb), as defined above, b) one monomer of formula (Ib), as defined above, wherein p=1, q=0, $R_3$ and $R_4$ which are identical or different, are each chosen from hydrogen and ($C_1$–$C_5$) alkyl groups and $R_5$ is chosen from ($C_9$–$C_{24}$)alkyl groups, and c) one monomer of formula (IIb), as defined above, wherein $R_3$ and $R_4$ which are each identical or different, are each chosen from hydrogen and ($C_1$–$C_5$)alkyl groups.

In one specific embodiment of the invention, the terpolymers comprise by weight, 40% to 95% of one monomeric (a) unit, 0.1% to 55% of one monomeric (c) unit, and 0.25% to 50% of one monomeric (b) unit. Representative terpolymers are described in patent application WO 00/68282, the disclosure of which related to terpolymers is specifically incorporated by reference herein.

Non-limiting examples of cationic poly(vinyllactam) polymers according to the invention may be chosen, for example, from vinylpyrrolidone/dimethylamino-propylmethacrylamide/dodecyldimethylmethacryl-amidopropylammonium tosylate terpolymers, vinyl-pyrrolidone/dimethylaminopropylmethacrylamide/cocoyldimethylmethacrylamidopropylammonium tosylate terpolymers, vinylpyrrolidone/dimethylaminopropyl-methacrylamide/lauryldimethylmethacrylamidopropyl-ammonium tosylate terpolymers, and vinylpyrrolidone/dimethylaminopropyl-methacrylamide/lauryldimethylmeth-acrylamidopropylammonium chloride terpolymers.

The weight-average molecular mass of the cationic poly (vinyllactam) polymers according to the present invention may range from 500 to 20,000,000, such as for example from 200,000 to 2,000,000 and further still from 400,000 to 800,000.

The Acrylic Terpolymers

Among the cationic amphiphilic polymers which may be utilized in the invention, mention may also be made of acrylic terpolymers, for example, those described in patent application EP-1 090 623 (the disclosure of which related to terpolymers is specifically incorporated by reference herein) and formed from:

(a) an acrylate monomer (a) chosen from ($C_1$–$C_6$)alkyl acrylates and ($C_1$–$C_6$)alkyl methacrylates, wherein said acrylate monomer (a) ranges from 5% to 80% by weight, such as for example from 15% to 70% by weight and further still from 40% to 70% by weight;

(b) a monomer (b) chosen from heterocyclic vinyl compounds containing at least one atom chosen from nitrogen and sulfur, (meth)acrylamides, mono($C_1$–$C_4$)alkylamino($C_1$–$C_4$)alkyl (meth)acrylates, di($C_1$–$C_4$)alkylamino($C_1$–$C_4$)alkyl (meth)acrylates, mono ($C_1$–$C_4$)alkylamino($C_1$–$C_4$)alkyl(meth)acrylamides and di($C_1$–$C_4$)alkylamino($C_1$–$C_4$)alkyl(meth)acrylamides, wherein said monomer (b) ranges from 5% to 80% by weight, such as from 10% to 70% by weight, and further still from 20% to 60% by weight;

a monomer (c) chosen from:

(i) a urethane formed from a monoethylenic unsaturated isocyanate and a nonionic surfactant with a ($C_{1-6}$)alkoxy end, (ii) a block copolymer formed from 1,2-butylene oxide and of 1,2-ethylene oxide, (iii) a copolymerizable ethylenic unsaturated surfactant monomer obtained by condensation of a nonionic surfactant with an α,β-ethylenic unsaturated carboxylic acid or its anhydride, (iv) a surfactant monomer (iv) chosen for example from the products formed, such as a urea, from a mono-ethylenic unsaturated monoisocyanate with a nonionic surfactant containing an amine function, (v) a monomer chosen from (meth)allyl ethers of formula $CH_2=CR_1CH_2OA_mB_nA_pR_2$, wherein $R_1$ is chosen from a hydrogen atom and a methyl group, A is chosen from a propylenoxy group and a butylenoxy group, B is an ethylenoxy group, n is chosen from zero and integers less than or equal to 200, such as, for example, less than or equal to 100, m and p, which are identical or different are each chosen from zero and integers less than n, and $R_2$ is a hydrophobic group of at least 8 carbon atoms such as for example, 8 to 30 carbon atoms, and (vi) a nonionic monomer of urethane type formed from a monohydric nonionic surfactant with a monoethylenic unsaturated isocyanate, wherein said monomer (c) ranges from 0.1% to 30% by weight, such as for example, 0.1% to 10% by weight;

further wherein the weight percentages of said above defined monomers are based on the total weight of said monomers forming the acrylic terpolymer.

Representative of the acrylate monomers (a) are those chosen from ($C_2$–$C_6$)alkyl acrylates, such as for example, ethyl acrylate.

Representative of the monomers (b) are those chosen from N,N-dimethylaminoethyl methacrylate (DMAEMA), N,N-diethylaminoethyl acrylate, N,N-diethylaminoethyl methacrylate, N-t-butylaminoethyl acrylate, N-t-butylaminoethyl methacrylate, N,N-dimethylaminopropylacrylamide, N,N-dimethylaminopropylmethacrylamide, N,N-diethylaminopropylacrylamide and N,N-diethylaminopropylmethacrylamide.

In one embodiment, the monomer (b) is N,N-dimethylaminoethyl methacrylate.

Representative of the monomers (c) are those chosen from copolymerizable ethylenic unsaturated surfactant monomers formed by condensing a nonionic surfactant with an $\alpha,\beta$-ethylenic unsaturated carboxylic acid or its anhydride, such as for example, $(C_3–C_4)$monocarboxylic acids, dicarboxylic acids and their anhydrides and further still, acrylic acid, methacrylic acid, crotonic acid, maleic acid, maleic anhydride as well as itaconic acid and itaconic anhydride.

Further non-limiting examples of the monomers (c) may be chosen from copolymerizable ethylenic unsaturated surfactant monomers formed by condensing a nonionic surfactant with itaconic acid. Nonionic surfactants which may be mentioned include, for example, $(C_{10}–C_{30})$fatty alcohols alkoxylated with 2 to 100 mol of an alkylene oxide, such as for example, 5 to 50 mol of an alkylene oxide. Non-limiting examples of these compounds comprise for example, polyethylene glycol ethers of $(C_{10}–C_{30})$fatty alcohols and further still, polyethylene glycol ethers of cetyl alcohol which are known as CETETH in the CTFA dictionary, 7th edition, 1997.

Conventional methods for preparing these acrylic terpolymers are known to those skilled in the art. Such methods include solution polymerization, precipitation polymerization and emulsion polymerization. Terpolymers in accordance with the invention and methods for preparing them are described for example, in patent applications EP-A-0 824 914 and EP-A-0 825 200 the disclosures of both of which relating to terpolymers and method for preparing them are specifically incorporated by reference, herein.

In one embodiment of the invention, the terpolymer is the "Structure Plus®" polymer sold by the company National Starch, which is formed from $(C_{10}–C_{30})$alkyl acrylates, amino (meth)acrylates and itaconate, polyoxyethylenated with 20 mol of ethylene oxide, in the form of an aqueous dispersion containing 20% Active Material.

In addition to the above-mentioned monomers, the terpolymers utilized in the invention may further comprise additional monomers that allow the said terpolymers to be crosslinked. These monomers may be used in relatively low proportions, up to 2% by weight relative to the total weight of the monomers used to prepare the terpolymers. Non-limiting examples of such crosslinking monomers may be chosen, for example, from aromatic monomers bearing several vinyl substituents, alicyclic monomers bearing several vinyl substituents, bifunctional esters of phthalic acid, bifunctional esters of methacrylic acid, multifunctional esters of acrylic acid, N-methylenebisacrylamide and aliphatic monomers bearing several vinyl substituents such as dienes, trienes and tetraenes.

Representative crosslinking monomers which may be used in accordance with the invention are chosen from divinylbenzenes, trivinylbenzenes, 1,2,4-trivinylcyclohexene, 1,5-hexadiene, 1,5,9-decatriene, 1,9-decadiene, 1,5-heptadiene, diallyl phthalates, ethylene glycol dimethacrylate, polyethylene glycol dimethacrylates, pentaacrylates, tetraacrylates, triallyl pentaerythritols, octaallyl sucroses, cycloparaffins, cycloolefins and N-methylenebisacrylamide.

In one embodiment of the invention, the at least one cationic amphiphilic polymer comprising at least one fatty chain is chosen from:

(i) quaternized celluloses modified with at least one group comprising at least one fatty chain, wherein said at least one group is chosen from alkyl groups, arylalkyl groups, and alkylaryl groups and contains at least 8 carbon atoms;

(ii) quaternized hydroxyethylcelluloses modified with at least one group comprising at least one fatty chain, wherein said at least one group is chosen from alkyl groups, arylalkyl groups, and alkylaryl groups and contains at least 8 carbon atoms;

(iii) cationic amphiphilic polyurethanes with at least one hydrophobic group comprising from 10 to 30 carbon atoms, (iv) cationic amphiphilic polyvinyllactams, and (v) an acrylic terpolymer formed from $(C_{10}–C_{30})$alkyl acrylates, amino(meth)acrylates and itaconate polyoxyethylenated with 20 mol of ethylene oxide.

In the present invention, the at least one cationic amphiphilic polymer comprising at least one fatty chain may be present in the composition in an amount ranging, for example from 0.01% to 3% by weight relative to the total weight of the dye composition, such as from 0.02% to 0.5% by weight relative to the total weight of the dye composition.

Oxyalkylenated Fatty Alcohols and Glycerolated Fatty Alcohols

The expression "oxyalkylenated fatty alcohol" is understood to mean any fatty alcohol of the following formula (IAA), such as a fatty alcohol that is at least substantially pure:

(IAA)

wherein:

R is chosen from optionally saturated, linear and branched groups containing from 8 to 40 carbon atoms such as for example, from 8 to 30 carbon atoms, Z is chosen from oxyethylenated groups and oxypropylenated groups of formulae (i), $(ii)_1$, and $(ii)_2$:

m is a number ranging from 1 to 250 and for example ranging from 2 to 100.

The expression "glycerolated fatty alcohol" is understood to mean any fatty alcohol of formula (IBB), such as any at least substantially pure fatty alcohol:

(IBB)

wherein:

R is chosen from optionally saturated, linear and branched groups containing from 8 to 40 carbon atoms such as for example, from 8 to 30 carbon atoms, Z is chosen from glycerolated groups of formula (iii):

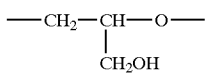

n is a number ranging from 1 to 30, such as for example from 1 to 10.

The composition according the invention may comprise mixtures of these oxyalkylenated and glycerolated fatty alcohols.

Non-limiting examples of oxyalkylenated fatty alcohols may be chosen from optionally saturated, linear and branched fatty alcohols containing from 10 to 20 carbon atoms and from 2 to 40 ethylene oxide groups.

Representative oxyalkylenated fatty alcohol type compounds, include those chosen from the following commercial products:

MERGITAL LM2 (Cognis) [lauryl alcohol 2EO];
IFRALAN L12 (Ifrachem) and REWOPAL 12 (Goldschmidt) [lauryl alcohol 12 EO];
EMPILAN KA 2.5/90FL (Albright & Wilson) and MERGITAL BL309 (Cognis) [decyl alcohol 3 EO];
EMPILAN KA 5/90FL (Albright & Wilson) and MERGITAL BL589 (Cognis) [decyl alcohol 5 EO];
BRIJ 58 (Uniquema) and SIMULSOL 58 (Seppic) [cetyl alcohol 20 EO];
EUMULGIN 05 (Cognis) [oleocetyl alcohol 5 EO];
MERGITAL OC30 (Cognis) [oleocetyl alcohol 30 EO];
BRIJ 72 (Uniquema) [stearyl alcohol 2 EO];
BRIJ (Uniquema) [stearyl alcohol 10 EO];
BRIJ 78P (Uniquema) [stearyl alcohol 20 EO];
BRIJ 700 (Uniquema) [stearyl alcohol 100 EO];
EUMULGIN B1 (Cognis) [cetylstearyl alcohol 12 EO];
EUMULGIN L (Cognis) [cetyl alcohol 9 EO and 2 PO]; and
WITCONOL APM (Goldschmidt) [myristyl alcohol 3 PO].

Non-limiting representatives of glycerolated fatty alcohol type compounds may be chosen, for example from lauryl alcohol containing 4 mol of glycerol (INCI name: Polyglyceryl-4 lauryl ether), oleyl alcohol containing 4 mol of glycerol (INCI name: Polyglyceryl-4 oleyl ether), oleyl alcohol containing 2 mol of glycerol (INCI name: Polyglyceryl-2 oleyl ether), cetearyl alcohol containing 2 mol of glycerol, cetearyl alcohol containing 6 mol of glycerol, oleocetyl alcohol containing 6 mol of glycerol, and octadecanol containing 6 mol of glycerol.

In one embodiment of the invention, the fatty alcohols may comprise a mixture of fatty alcohols. That is, it is possible for several fatty alcohol species chosen from oxyalkylenated fatty alcohols and glycerolated fatty alcohols to coexist in the form of a mixture in one commercial product.

The oxyalkylenated fatty alcohols and glycerolated fatty alcohols may be present in the composition according to the invention in an amount, for example, ranging from 0.05% to 50% by weight relative to the total weight of the composition, such as, for further example, from 2% to 40% by weight relative to the total weight of the composition.

At Least One Hydroxylated Solvent

For the purposes of the invention, the term "hydroxylated solvent" is understood to be chosen from optionally saturated, cyclic, linear and branched compounds bearing at least one —OH function.

In one embodiment of the invention, the at least one hydroxylated solvent may comprise for example, from 2 to 12 carbon atoms, such as from 2 to 8 carbon atoms. Further in one specific embodiment, the at least one hydroxylated solvent comprises 2 or 3 carbon atoms.

The at least one hydroxylated solvent used according to the present invention may be chosen for example from ethyl alcohol, propyl alcohol, n-butyl alcohol, ($C_2$–$C_6$)polyols such as 2-methyl-1,3-butanediol, 2,2-dimethyl-1,3-propanediol, 2-methyl-1,3-propanediol, 2-methyl-2,4-pentanediol, 1,5-pentanediol, 3-methyl-1,5-pentanediol and further still, glycerol, propylene glycol, dipropylene glycol and 1,3-propanediol.

Polyol ethers may also be used according to the invention, provided that they contain at least one free hydroxyl function. Non-limiting examples of polyol ethers may be chosen for example from ($C_1$–$C_8$)ethers of ($C_2$–$C_9$)glycols.

Among the ($C_1$–$C_8$)ethers of a ($C_2$–$C_9$)glycol, mention may be made for example of:

(i) ($C_1$–$C_8$)ethers of a ($C_2$)glycol such as, for example, ($C_4$–$C_8$)alkyl ethers of a ($C_2$)glycol, such as ethylene glycol monobutyl ether, and ($C_6$–$C_8$)aryl ethers of a ($C_2$)glycol, such as ethylene glycol monophenyl ether and ethylene glycol monobenzyl ether, (ii) ($C_1$–$C_8$)ethers of a ($C_3$–$C_9$)glycol, chosen for example from:
  (a) ($C_1$–$C_8$)alkyl ethers of a ($C_3$–$C_9$)glycol, chosen from propylene glycol monomethyl ether, propylene glycol monoethyl ether, diethylene glycol monomethyl ether and monoethyl ether, dipropylene glycol monomethyl ether and tripropylene glycol monomethyl ether, and
  (b) ($C_6$–$C_8$)aryl ethers of a $C_3$–$C_9$ glycol, chosen from propylene glycol monophenyl ether, propylene glycol monobenzyl ether, diethylene glycol monophenyl ether and diethylene glycol monobenzyl ether.

An at least one hydroxylated solvent having a molecular weight of less than 250 may be present in the composition in accordance with the invention in an amount, for example, ranging from 0.01% to 25% by weight relative to the total weight of the composition, such as from 0.1% to 20% by weight relative to the total weight of the composition.

In the composition in accordance with the invention, the weight ratio between the at least one compound chosen from oxyalkylenated fatty alcohols and glycerolated fatty alcohols, and the at least one hydroxylated solvent is greater than 1:1, such as for example, ranging from greater than 1:1 to 30:1 and further still, ranging from 1.5:1 to 20:1.

Oxidation Dyes

The at least one oxidation dye which can be used according to the present invention is chosen from oxidation bases, and oxidation couplers. In one embodiment, the compositions can comprise at least one oxidation base.

The oxidation bases usable in the context of the present invention are chosen from those conventionally known as oxidation dyes. Representative oxidation dyes include ortho-phenylenediamines, para-phenylenediamines, double bases, ortho-aminophenols, para-aminophenols, heterocyclic bases and their acid addition salts.

For example, the following oxidation bases may be used:

(I) para-phenylenediamines chosen from compounds of formula (I), and their acid addition salts:

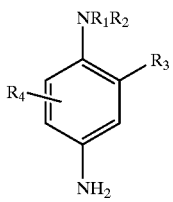

(I)

wherein:

- $R_1$ is chosen from hydrogen, $C_1$–$C_4$ alkyl groups, monohydroxy($C_1$–$C_4$ alkyl) groups, polyhydroxy ($C_2$–$C_4$ alkyl) groups, ($C_1$–$C_4$)alkoxy($C_1$–$C_4$)alkyl groups, phenyl groups, 4'-aminophenyl groups, and $C_1$–$C_4$ alkyl groups substituted with at least one group chosen from nitrogen-containing groups,
- $R_2$ is chosen from hydrogen, $C_1$–$C_4$ alkyl groups, monohydroxy($C_1$–$C_4$ alkyl) groups, polyhydroxy ($C_2$–$C_4$ alkyl) groups, ($C_1$–$C_4$)alkoxy($C_1$–$C_4$)alkyl groups, and $C_1$–$C_4$ alkyl groups substituted with a substituent chosen from nitrogen-containing groups;
- $R_1$ and $R_2$ may also form, together with the nitrogen to which they are bonded, a 5-or 6-membered nitrogen-containing heterocycle ring, optionally substituted with, for example, at least one group chosen from alkyl groups, hydroxyl groups and ureido groups;
- $R_3$ is chosen from hydrogen, halogens, such as chlorine, $C_1$–$C_4$ alkyl groups, sulfo groups, carboxyl groups, monohydroxy($C_1$–$C_4$ alkyl) groups, hydroxy($C_1$–$C_4$ alkyoxy) groups, acetylamino($C_1$–$C_4$ alkoxy) groups, mesylamino($C_1$–$C_4$ alkoxy) groups, and carbamoylamino($C_1$–$C_4$ alkoxy) groups;
- $R_4$ is chosen from hydrogen, halogens, and $C_1$–$C_4$ alkyl groups.

Suitable nitrogen-containing groups of formula (I) above may, for example, be chosen from amino,($C_1$–$C_4$) monoalkylamino, di($C_1$–$C_4$)alkylamino, tri($C_1$–$C_4$) alkylamino, monohydroxy($C_1$–$C_4$)alkylamino, imidazolinium, and ammonium groups.

Representative para-phenylenediamines of formula (I) above which may be used include para-phenylenediamine, para-toluylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-amino-N,N-bis(β-hydroxyethyl)-3-methylaniline, 4-amino-3-chloro-N,N-bis(β-hydroxyethyl) aniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxy-methyl-para-phenylenediamine, N,N-dimethyl-3-methyl-para-phenylenediamine, N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine and 2-β-hydroxyethyloxy-para-phenylenediamine, and their acid addition salts.

In other embodiments of the present invention, para-phenylenediamines of formula (I) above can, for example, be chosen from para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, and their acid addition salts.

According to the invention, "double bases" is understood to mean the compounds comprising at least two aromatic rings on which at least one functional group chosen from amino groups and hydroxyl groups are carried.

(II) Representative double bases chosen from compounds comprising at least two aromatic rings substituted with at least one group chosen from amino and hydroxyl groups may include double bases chosen from compounds of formula (II), and their acid addition salts:

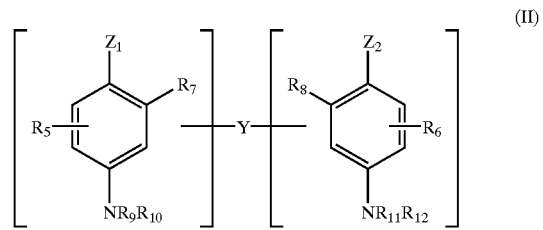

(II)

wherein:

- $Z_1$ and $Z_2$, which may be identical or different, are each chosen from hydroxyl groups, and —$NH_2$ groups, optionally substituted with a group chosen from $C_1$–$C_4$ alkyl groups, and linkers Y
- linker Y is chosen from linear and branched, divalent alkylene groups comprising from 1 to 14 carbon atoms, optionally interrupted by, or optionally terminating with, at least one entity chosen from nitrogen-containing groups and heteroatoms such as oxygen, sulfur, and nitrogen, and optionally substituted with at least one group chosen from hydroxyl groups, and $C_1$–$C_6$ alkoxy groups;
- $R_5$ and $R_6$, which may be identical or different, are each chosen from hydrogen, halogens, $C_1$–$C_4$ alkyl groups, monohydroxy($C_1$–$C_4$ alkyl) groups, polyhydroxy ($C_2$–$C_4$ alkyl) groups, amino($C_1$–$C_4$ alkyl) groups, and linkers Y;
- $R_7$, $R_8$, $R_9$, $R_{10}$, $R_{11}$ and $R_{12}$, which may be identical or different, are each chosen from hydrogen, linkers Y, and $C_1$–$C_4$ alkyl groups;
- provided that said compounds of formula (II) comprise only one linker Y per molecule.

Suitable nitrogen-containing groups of formula (II) include mono($C_1$–$C_4$)alkylamino, di($C_1$–$C_4$)alkylamino, tri ($C_1$–$C_4$)alkylamino, monohydroxy($C_1$–$C_4$)alkylamino, imidazolinium and ammonium groups.

Representative double bases of formula (II) include N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)-tetramethylenediamine, N,N'-bis(β-hydroxyethyl)-N,N'-bis (4-aminophenyl)tetramethylenediamine, N,N'-bis(4-methylaminophenyl)tetramethylene-diamine, N,N'-bis (ethyl)-N,N'-bis(4'-amino-3'-methylphenyl) ethylenediamine, 1,8-bis(2,5-diaminophenoxy)-3,5-dioxaoctane, and their acid addition salts.

In another embodiment of the invention, the double bases of formula (II) may be chosen from N,N'-bis(β-hydroxyethyl)-N,N'-bis(4'-aminophenyl)-1,3- diaminopropanol, 1,8-bis(2,5-diaminophenoxy)-3,5-dioxaoctane, and their acid addition salts.

(III) para-aminophenols can be chosen from compounds of formula (III), and their acid addition salts:

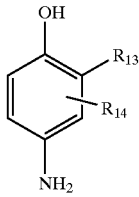

(III)

wherein:

$R_{13}$ is chosen from hydrogen, halogens, such as fluorine, $C_1$–$C_4$ alkyl groups, monohydroxy($C_1$–$C_4$ alkyl) groups, ($C_1$–$C_4$)alkoxy($C_1$–$C_4$)alkyl groups, amino ($C_1$–$C_4$ alkyl), and hydroxy($C_1$–$C_4$)alkylamino($C_1$–$C_4$ alkyl) groups;

$R_{14}$ is chosen from hydrogen, halogens, such as fluorine, $C_1$–$C_4$ alkyl groups, monohydroxy($C_1$–$C_4$ alkyl) groups, polyhydroxy($C_2$–$C_4$ alkyl) groups, amino ($C_1$–$C_4$ alkyl) groups, cyano($C_1$–$C_4$ alkyl) groups, and ($C_1$–$C_4$)alkoxy($C_1$–$C_4$)alkyl groups.

Representative para-aminophenols of formula (III) above include para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, and their acid addition salts.

(IV) ortho-aminophenols can be chosen, for example, from 2-aminophenol, 2-amino-1-hydroxy-5-methylbenzene, 2-amino-6-methylbenzene, 5-acetamido-2-aminophenol, and their acid addition salts.

(V) heterocyclic bases can be chosen, for example, from pyridine derivatives, pyrimidine derivatives, pyrazole derivatives, pyrazolo-pyrimidine derivatives, and their acid addition salts.

Representative pyridine derivatives include 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine, 3,4-diaminopyridine, and their acid addition salts. Some of the aforementioned pyridine derivatives have been described, for example in the patents GB 1,026,978 and GB 1,153,196, the disclosures of which related to pyridine derivatives are specifically incorporated by reference herein.

Representative pyrimidine derivatives include 2,4,5,6-tetra-aminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine, and their acid addition salts.

Representative pyrazolo-pyrimidine derivatives include those described, for example, in the patent application FR-A-2 750 048, the disclosure of which related to pyrazolo-pyrimidine derivatives is specifically incorporated by reference herein. Such pyrazolo-pyrimidine derivatives include pyrazolo[1,5-a]pyrimidines, such as
pyrazolo[1,5-a]pyrimidine-3,7-diamine;
2,5-dimethylpyrazolo[1,5-a]pyrimidine-3,7-diamine;
pyrazolo[1,5-a]pyrimidine-3,5-diamine;
2,7-dimethylpyrazolo[1,5-a]pyrimidine-3,5-diamine;
3-aminopyrazolo[1,5-a]pyrimidin-7-ol;
3-aminopyrazolo[1,5-a]pyrimidin-5-ol;
2-(3-aminopyrazolo[1,5-a]pyrimidin-7-ylamino)ethanol;
2-(7-aminopyrazolo[1,5-a]pyrimidin-3-ylamino)ethanol;
2-[(3-aminopyrazolo[1,5-a]pyrimidin-7-yl)-(2-hydroxyethyl)amino]ethanol;
2-[(7-aminopyrazolo[1,5-a]pyrimidin-3-yl)-(2-hydroxyethyl)amino]ethanol;
5,6-dimethylpyrazolo[1,5-a]pyrimidine-3,7-diamine;
2,6-dimethylpyrazolo[1,5-a]pyrimidine-3,7-diamine;
2,5,N7,N7-tetramethylpyrazolo[1,5-a]pyrimidine-3,7-diamine; their salts, such as their acid addition salts, and their tautomeric forms when a tautomeric equilibrium exists.

Representative pyrazole derivatives include 4,5-diamino-1-methylpyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-hydroxyethylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, and their acid addition salts. Some of the aforementioned pyrazole derivatives have been described, for example in Patents DE 3,843,892, DE 4,133,957 and Patent Applications WO 94/08969, WO 94/08970, FR-A-2,733,749 and DE 195 43 988, the disclosures of which related to pyrazole derivatives are specifically incorporated by reference herein.

In accordance with the present invention, the oxidation bases are generally present in an amount ranging for example from 0.0005% to 12% by weight, relative to the total weight of the composition, such as from 0.005% to 8%.

Suitable couplers which may be used in the dyeing process of the invention include couplers conventionally used in oxidation dyeing compositions. Such couplers can be chosen, for example, from meta-phenylene-diamines, meta-aminophenols, meta-diphenols, naphthols, such as monohydroxylated naphthalene derivatives and polyhydroxylated naphthalene derivatives, sesamol and its derivatives, heterocyclic couplers, such as, for example, indole derivatives, indoline derivatives, pyridine derivatives, and their acid addition salts.

Representative couplers include 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole, 3-(4-hydroxy-1-methyl-1H-indol-5-ylmethyl)-1-methylpyridinium, 6-hydroxyindoline, 2,6-dihydroxy-4-methylpyridine, 1-H-3-methylpyrazol-5-one, 1-phenyl-3-methylpyrazol-5-one, and their acid addition salts.

When these couplers are present, they are generally present in an amount ranging for example from 0.0001% to 10% by weight, relative to the total weight of the composition, such as from 0.005% to 5%.

Generally, the acid addition salts of the oxidation bases and couplers can be chosen from hydrochlorides, hydrobromides, sulfates, tartrates, lactates and acetates.

The compositions according to the invention may also comprise at least one direct dye. Representative direct dyes which can be used in the present invention include direct dyes that have conventionally been used in direct dyeing compositions and lighting direct dyeing compositions. For example, the dyes can be chosen from neutral, cationic, and anionic nitro dyes, neutral, cationic, and anionic anthraquinone dyes, and neutral, cationic, and anionic azo dyes. Generally, the direct dyes are present in amounts ranging for example from 0.001% to 20% by weight of the total weight of the composition, such as for example from 0.01% to 10% by weight of the total weight of the composition.

In one embodiment of the invention, namely within the ready-to-use composition, said at least one composition (A) and said at least one composition (B) can further comprise at least one polymer chosen from cationic and amphoteric polymers, such as substantive polymers.

Cationic Polymers

As used herein, "cationic polymer" refers to polymers chosen from polymers comprising at least one cationic group and polymers comprising at least one group which can be ionized to form cationic groups.

Representative cationic polymers which may be used in accordance with the present invention include any of those already known to improve at least one cosmetic property of hair, such as, for example, those described in patent application EP-A-0 337 354 and in French patent applications FR-A-2 270 846, 2 383 660, 2 598 611, 2 470 596 and 2 519 863, the disclosures of which relating to cationic polymers are specifically incorporated herein by reference.

According to the present invention, the at least one cationic polymer may be chosen from polymers comprising units chosen from primary amine groups, secondary amine groups, tertiary amine groups and quaternary amine groups, wherein said groups form part of the polymer skeleton, or are part of at least one lateral substituent on said polymer skeleton.

According to the present invention, the at least one cationic polymer has a number-average molecular mass generally ranging for example from 500 to $5\times10^6$, such as from $1\times10^3$ to $3\times10^6$.

The at least one cationic polymer may, for example, be chosen from polymers of quaternary polyammonium type, polymers of polyamino amide type and polymers of polyamine type. Such types of polymers are known in the art. They are for example described in French patents Nos. 2,505,348 and 2,542,997, the disclosures of which relating to such polymers are specifically incorporated by reference herein.

(1) homopolymers and copolymers derived from monomers chosen from acrylic esters, methacrylic esters, and amides and comprising at least one of the units of formula (I), (II), (III) or (IV) below:

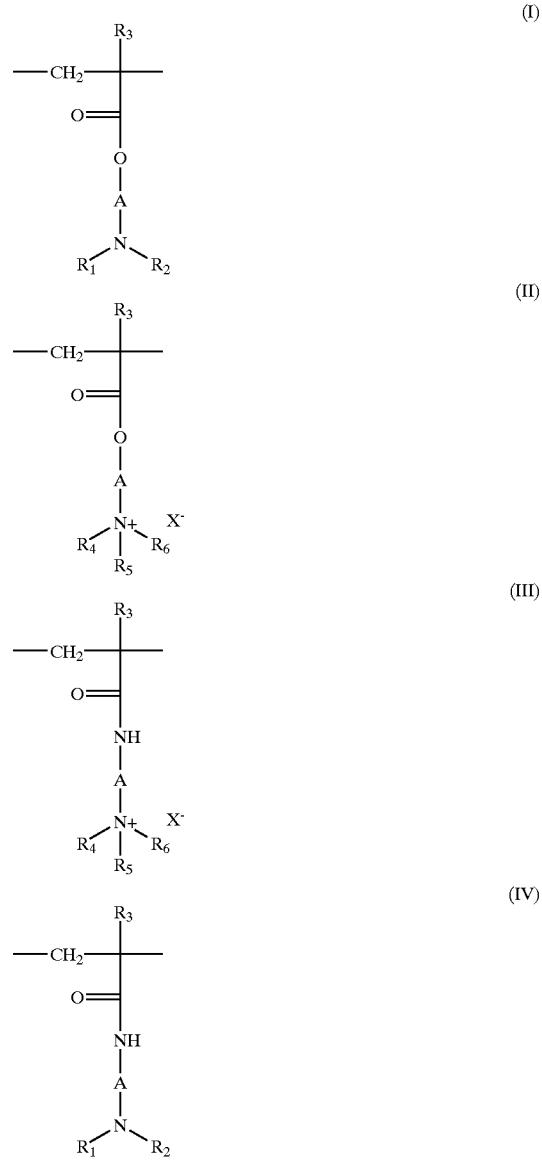

wherein:
$R_3$, which may be identical or different, are each chosen from hydrogen and a methyl group;
A, which may be identical or different, are each chosen from linear and branched ($C_1$–$C_6$)alkyl groups, such as ($C_2$–$C_3$)alkyl groups, and ($C_1$–$C_4$)hydroxyalkyl groups;
$R_4$, $R_5$ and $R_6$, which may be identical or different, are each chosen from ($C_1$–$C_{18}$)alkyl groups, such as, ($C_1$–$C_6$), and a benzyl group;
$R_1$ and $R_2$, which may be identical or different, are each chosen from hydrogen and ($C_1$–$C_6$)alkyl groups, such as a methyl group and an ethyl group;
$X^-$ is an anion chosen from anions derived from at least one inorganic acid and anions derived from at least one organic acid, such as a methylsulfate anion and halides, such as chloride and bromide.

(1) homo- and copolymers of family (1) may further comprise at least one unit derived from at least one comonomer chosen from vinyllactams, vinyl esters, acrylamides, methacrylamides, diacetone acrylamides, acrylamides and methacrylamides substituted on the nitrogen with at least one group chosen from ($C_1$–$C_4$)alkyls, acrylic acids, methacrylic acids, acrylic esters, and methacrylic esters. Non-limiting examples of vinyllactams include vinylpyrrolidone and vinylcaprolactam.

Non-limiting examples of copolymers of family (1) include:

copolymers derived from (i) acrylamide and (ii) dimethylaminoethyl methacrylate quaternized with at least one group chosen from a dimethylsulfate group and dimethylhalides, such as the product sold under the name HERCOFLOC by the company Hercules;

copolymers derived from (i) acrylamide and (ii) methacryloyloxy-ethyltrimethylammonium chloride described, for example, in patent application EP-A-080 976, the disclosure of which relating to such copolymers is specifically incorporated herein by reference, and which is sold under the name BINA QUAT P 100 by the company Ciba Geigy;

copolymers derived from (i) acrylamide and (ii) methacryloyloxy-ethyltrimethylammonium methosulfate, such as, for example, copolymers sold under the name RETEN by the company Hercules;

quaternized and non-quaternized vinylpyrrolidone/dialkylaminoalkyl acrylate copolymers and quaternized and non-quaternized vinylpyrrolidone/dialkylaminoalkyl methacrylate copolymers, such as the products sold under the name "GAFQUAT" by the company ISP, such as, for example, "GAFQUAT 734" or "GAFQUAT 755" and the products known as "COPOLYMER 845, 958 and 937". These polymers are described in detail in French patents 2 077 143 and 2 393 573, the disclosures of which relating to such copolymers are specifically incorporated herein by reference;

dimethylaminoethyl methacrylate/vinylcaprolactam/vinylpyrrolidone terpolymers, such as the product sold under the name GAFFIX VC 713 by the company ISP;

vinylpyrrolidone/methacrylamidopropyldimethylamine copolymers, such as the product sold under the name STYLEZE CC 10 by ISP; and quaternized vinylpyrrolidone/dimethylaminopropylmethacrylamide copolymers, such as the product sold under the name "GAFQUAT HS 100" by the company ISP;

(2) cellulose ether derivatives comprising quaternary ammonium groups, such as those described in French patent 1,492,597, the disclosure of which relating to the cellulose ether derivatives is specifically incorporated herein by reference, and polymers sold under the names "JR" (JR 400, JR 125 and JR 30M) and "LR" (LR 400, or LR 30M) by the company Union Carbide Corporation. These polymers are also defined in the CTFA dictionary as quaternary ammoniums of hydroxyethylcellulose which have reacted with an epoxide substituted with a trimethylammonium group;

(3) cationic cellulose derivatives such as cellulose copolymers and cellulose derivatives grafted with at least one water-soluble monomer of quaternary ammonium, such as those described in U.S. Pat. No. 4,131,576, the disclosure of which relating to such cationic cellulose derivatives is specifically incorporated herein by reference, such as hydroxyalkylcelluloses (such as, for example, hydroxymethylcelluloses, hydroxyethylcelluloses and hydroxypropylcelluloses, wherein said hydroxyalkylcelluloses are grafted with at least one salt chosen from, for example, methacryloylethyltrimethylammonium salts, methacrylamidopropyltrimethylammonium salts and dimethyldiallylammonium salts). For example, commercial products corresponding to the aforementioned cationic cellulose derivatives include the products sold under the names "CELQUAT L 200" and "CELQUAT H 100" by the company National Starch;

(4) cationic polysaccharides, such as those described in U.S. Pat. Nos. 3,589,578 and 4,031,307, the disclosures of which relating to such cationic polysaccharides are incorporated herein by reference, such as guar gums comprising at least one cationic trialkylammonium group. For example, guar gums modified with at least one salt, such as a chloride salt, of 2,3-epoxypropyltrimethylammonium may be used in the present invention. Such products are sold in particular under the trade names JAGUAR C13 S, JAGUAR C 15, JAGUAR C 17 and JAGUAR C162 by the company Meyhall;

(5) polymers comprising (i) piperazinyl units and (ii) at least units chosen from divalent alkylene groups and divalent hydroxyalkylene groups, wherein said at least one unit optionally comprises at least one chain chosen from straight chains and branched chains, wherein said at least one chain is optionally interrupted by at least one entity chosen from oxygen, sulfur, nitrogen, aromatic rings and heterocyclic rings, the oxidation products of said polymers and the quaternization products of said polymers. For example, such polymers are described in French patents 2,162,025 and 2,280,361, the disclosures of which relating to such polymers are specifically incorporated herein by reference;

(6) water-soluble polyamino amides which may be prepared by polycondensation reaction of an acidic compound with a polyamine compound, wherein said polyamino amides may be crosslinked with at least one crosslinking agent chosen from epihalohydrins, diepoxides, dianhydrides, unsaturated dianhydrides, bis-unsaturated derivatives, bis-halohydrins, bis-azetidiniums, bis-haloacyldiamines, bis-alkyl halides and oligomers derived from reaction of at least one difunctional compound with at least one compound chosen from bis-halohydrins, bis-azetidiniums, bis-haloacyldiamines, bis-alkyl halides, epihalohydrins, diepoxides and bis-unsaturated derivatives, wherein said crosslinking agent may be used in a proportion generally ranging from 0.025 mol to 0.35 mol per amine group of said polyamino amide, wherein said polyamino amides may optionally be alkylated, and wherein if said polyamino amides comprise at least one tertiary amine group, said polyamino amides may optionally be quaternized. For example, such polymers are described in French patents 2,252,840 and 2,368,508, the disclosures of which relating to such polymers are specifically incorporated herein by reference;

(7) polyamino amide derivatives derived from condensation of at least one polyalkylene polyamine with at least one polycarboxylic acid, followed by alkylation with at least one bifunctional agent. Non-limiting examples of such polyamino amide derivatives include adipic acid/dialkylaminohydroxyalkyldialkylene-triamine polymers wherein said alkyl group is chosen from ($C_1$–$C_4$)alkyl groups, such as a methyl group, an ethyl group and a propyl group. For example, such polymers are described in French patent 1,583,363, the disclosure of which relating to such polymers is specifically incorporated herein by reference.

Other non-limiting examples of such derivatives include the adipic acid/dimethylaminohydroxypropyl/diethylenetriamine polymers sold under the name "CARTARETINE F, F4 or F8" by the company Sandoz.

(8) polymers derived from the reaction of (i) at least one polyalkylene polyamine comprising two primary amine groups and at least one secondary amine group with (ii) at least one dicarboxylic acid chosen from diglycolic acid and saturated aliphatic dicarboxylic acids comprising from 3 to 8 carbon atoms. According to the present invention, the molar ratio of the at least one polyalkylene polyamine to the at least one dicarboxylic acid generally ranges from 0.8:1 to 1.4:1. The polyamino amide resulting from the above reaction may be reacted with epichlorohydrin in a molar ratio of epichlorohydrin to the at least one secondary amine group of the polyamino amide generally ranging from 0.5:1 to 1.8:1. For example, such polymers are described in U.S. Pat. Nos. 3,227,615 and 2,961,347, the disclosures of which relating to such polymers are specifically incorporated herein by reference.

Polymers of this type are sold in particular under the name "HERCOSETT 57" by the company Hercules Inc. and under the name "PD 170" or "DELSETTE 101" by the company Hercules in the case of adipic acid/epoxypropyl/diethylenetriamine copolymers.

(9) cyclopolymers of alkyldiallylamine and cyclopolymers of dialkyldiallylammonium, such as homopolymers and copolymers comprising, as a constituent of the chain, units chosen from units of formulae (V) and (VI):

$$\text{—(CH}_2)_t\text{—CR}_9 \overset{(CH_2)_k}{\underset{\underset{R_7 \quad R_8}{\overset{|}{N+}}\quad Y^-}{\overset{H_2C}{\diagdown}\diagup \overset{CH_2}{\diagup}}} C(R_9)\text{—CH}_2\text{—} \quad (V)$$

$$\text{—(CH}_2)_t\text{—CR}_9 \overset{(CH_2)_k}{\underset{\underset{R_7}{\overset{|}{N}}}{\overset{H_2C}{\diagdown}\diagup \overset{CH_2}{\diagup}}} C(R_9)\text{—CH}_2\text{—} \quad (VI)$$

wherein:

k and t, which may be identical or different, are each chosen from 0 and 1, with the proviso that the sum of k+t is equal to 1;

$R_9$, which may be identical or different, are each chosen from hydrogen and a methyl group;

$R_7$ and $R_8$, which may be identical or different, are each chosen from alkyl groups comprising from $(C_1-C_{22})$ alkyl groups, such as, $(C_1-C_4)$alkyl groups, hydroxyalkyl groups, such as $(C_1-C_5)$hydroxyalkyl groups, and $(C_1-C_4)$amidoalkyl groups;

$R_7$ and $R_8$, together with the nitrogen cation to which they are commonly bonded, may additionally form at least one cationic heterocyclic group, such as a cationic piperidyl group and a cationic morpholinyl group;

$Y^-$ is an anion, such as a bromide anion, a chloride anion, an acetate anion, a borate anion, a citrate anion, a tartrate anion, a bisulfate anion, a bisulfite anion, a sulfate anion and a phosphate anion. For example, such polymers are described in French patent 2,080,759 and in its Certificate of Addition 2,190,406, the disclosures of which are relating to such polymers are specifically incorporated herein by reference.

Non-limiting examples of the (9) cyclopolymers defined above include the dimethyldiallylammonium chloride homopolymer sold under the name "MERQUAT 100" by the company Calgon (and its homologues of low weight-average molecular mass) and copolymers of diallyldimethylammonium chloride and of acrylamide, sold under the name "MERQUAT 550".

(10) quaternary diammonium polymers comprising repeating units of formula (VII):

$$\text{——}\underset{\underset{R_{14}}{|} X^-}{\overset{\overset{R_{13}}{|}}{N+}}\text{—A}_1\text{—}\underset{\underset{R_{16}}{|} X^-}{\overset{\overset{R_{15}}{|}}{N+}}\text{—B}_1\text{——} \quad (VII)$$

wherein:

$R_{13}$, $R_{14}$, $R_{15}$ and $R_{16}$, which may be identical or different, are each chosen from $(C_1-C_{20})$aliphatic, $(C_2-C_{22})$ alicyclic groups, $(C_5-C_{20})$arylaliphatic groups, and lower hydroxyalkyl groups; and additionally at least two of said $R_{13}$, $R_{14}$, $R_{15}$ and $R_{16}$, together with the nitrogen cations to which they are attached, may form at least one cationic heterocycle optionally comprising an additional heteroatom other than nitrogen; and additionally, $R_{13}$, $R_{14}$, $R_{15}$ and $R_{16}$, which may be identical or different, are each chosen from linear and branched $(C_1-C_6)$alkyl groups substituted with at least one group chosen from a nitrile group, ester groups, acyl groups, amide groups and groups chosen from groups of formulae —CO—O—$R_{17}$—D and —CO—NH—$R_{17}$—D wherein $R_{17}$ is chosen from alkylene groups and D is chosen from quaternary ammonium groups;

$A_1$ and $B_1$, which may be identical or different, are each chosen from linear and branched, saturated and unsaturated $(C_2-C_{20})$polymethylene groups, wherein said polymethylene groups may optionally comprise, optionally linked to and optionally intercalated in the main chain, at least one entity chosen from aromatic rings, oxygen, sulfur, sulfoxide groups, sulfone groups, disulfide groups, amino groups, alkylamino groups, hydroxyl groups, quaternary ammonium groups, ureido groups, amide groups and ester groups; and $X^-$ is an anion chosen from anions derived from inorganic acids and anions derived from organic acids; and $A_1$, $R_{13}$ and $R_{15}$ may optionally form, together with the nitrogen cations to which they are attached, at least one piperazine ring;

with the proviso that if $A_1$ is chosen from linear and branched, saturated and unsaturated $(C_2-C_{20})$ polymethylene groups and linear and branched, saturated and unsaturated hydroxy$(C_2-C_{20})$polymethylene groups, $B_1$ may also be chosen from groups of formula:

$$\text{—(CH}_2)_n\text{—CO—D—OC—(CH}_2)_n\text{—}$$

wherein:

n is a number ranging from 1 to 100, such as, from 1 to 50;

D is chosen from:
a) glycol residues of formula: —O—Z—O—, wherein Z is chosen from linear and branched hydrocarbon groups and groups chosen from groups of formulae:

$$\text{—(CH}_2\text{—CH}_2\text{—O)}_x\text{—CH}_2\text{—CH}_2\text{—;}$$

and $$\text{—[CH}_2\text{—CH(CH}_3)\text{—O]}_y\text{—CH}_2\text{—CH(CH}_3)\text{—;}$$

wherein x and y, which may be identical or different, are each chosen from integers ranging from 1 to 4 (in which case x and y represent a defined and unique degree of polymerization) and any number ranging from 1 to 4 (in which case x and y represent an average degree of polymerization);

b) bis-secondary diamine residues such as piperazine derivatives;

c) bis-primary diamine residues chosen from residues of formula: —NH—Y—NH—, wherein Y is chosen from linear and branched hydrocarbon groups and residues of formula —$CH_2$—$CH_2$—S—S—$CH_2$—$CH_2$—; and d) ureylene groups of formula: —NH—CO—NH—.

In one embodiment, $X^-$ is an anion chosen from a chloride anion and a bromide anion.

According to the present invention, the quaternary diammonium polymers have a number-average molecular mass generally ranging, for example, from 1000 to 100,000.

For example, polymers of this type are described in French Patent Nos. 2,320,330, 2,270,846, 2,316,271, 2,336,434 and 2,413,907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020, the disclosures of which relating to such polymers are specifically incorporated herein by reference.

Further, according to the present invention, polymers comprising repeating units of formula (VIII) may be used:

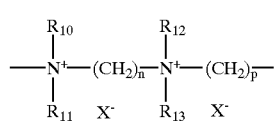

(VIII)

wherein:

$R_{10}$, $R_{11}$, $R_{12}$ and $R_{13}$, which may be identical or different, are each chosen from ($C_1$–$C_4$)alkyl groups and ($C_1$–$C_4$) hydroxyalkyl groups;

n and p, which may be identical or different, are each chosen from integers ranging from 2 to 20; and $X^-$ is an anion chosen from anions derived from inorganic acids and anions derived from organic acids.

(11) polyquaternary ammonium polymers comprising repeating units of formula (IX):

described in the U.S. Pat. Nos. 4,157,388, 4,390,689, 4,702,906, and 4,719,282, the disclosures of which relating to such preparation procedures are specifically incorporated by reference herein.

Among these, there may be mentioned for example the products "Mirapol A 15", "Mirapol AD1", "Mirapol AZ1" and Mirapol 175" sold by the company Miranol.

(12) quaternary polymers of vinylpyrrolidone and quaternary polymers of vinylimidazole, such as, for example, the products sold under the names LUVIQUAT FC 905, FC 550 and FC 370 by the company BASF.

(13) polyamines, such as POLYQUART H sold by Henkel under the reference name "POLYETHYLENE GLYCOL (15) TALLOW POLYAMINE" in the CTFA dictionary.

(14) crosslinked (meth)acryloyloxy($C_1$–$C_4$)alkyltri-($C_1$–$C_4$) alkylammonium salt polymers, such as the polymers derived from homopolymerization of dimethylaminoethyl methacrylate quaternized with methyl chloride and polymers derived from copolymerization, for example, of acrylamide with dimethylaminoethyl methacrylate quaternized with a methyl halide (such as methyl chloride), wherein the homo- or copolymerization is followed by crosslinking with at least one compound comprising olefinic unsaturation, such as methylenebisacrylamide. For example, a crosslinked acrylamide/methacryloyloxyethyltrimethylammonium chloride copolymer (20/80 by weight) in the form of a dispersion comprising 50% by weight of said copolymer in mineral oil may be used. This dispersion is sold under the name "SALCARE SC 92" by the company Allied Colloids. Further, a crosslinked methacryloyloxyethyltrimethylammonium chloride homopolymer comprising 50% by weight of the homopolymer in mineral oil or in a liquid ester may be used. These dispersions are sold under the names "SALCARE SC 95" and "SALCARE SC 96" by the company Allied Colloids.

The at least one polymer chosen from cationic polymers according to the present invention, may for example, be chosen from polyalkyleneimines (such as polyethyleneimines), polymers comprising vinylpyridine units, polymers comprising vinylpyridinium units, condensates of polyamines, condensates of epichlorohydrin, quaternary polyureylenes and chitin derivatives.

Other embodiments of the invention use cationic polymers chosen from the polymers of (1), (9), (10), (11) and (14). For example, polymers of formulae (W) and (U) can be used:

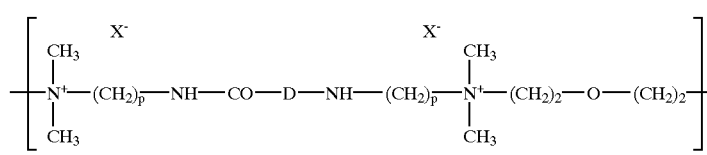

(IX)

wherein:

p is an integer ranging from 1 to 6,

D is chosen from a direct bond and —($CH_2$)$_r$—CO— groups, wherein r is a number equal to 4 or 7, and $X^-$ is an anion chosen from anions derived from inorganic acids and anions derived from organic acids.

For example, such compounds are described in patent application EP-A-122,324, the disclosure of which relating to such compounds is specifically incorporated by reference herein, and may be prepared according to the procedures

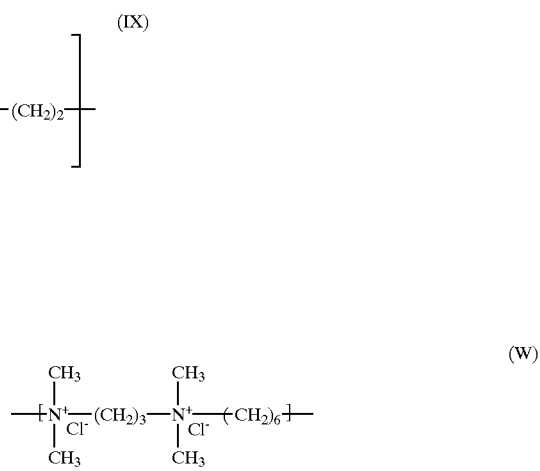

(W)

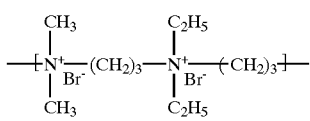

(U)

In one embodiment of the invention, the polymers of formula (W) have a weight-average molar mass, determined by gel permeation chromatography ranging from 9500 to 9900. In addition, in one embodiment of the invention, the polymers of formula (U) have a weight-average molar mass, determined by gel permeation chromatography of 1200.

The concentration of the at least one polymer chosen from cationic polymers other than the at least one cationic amphiphilic polymer of the present invention, in the composition according to the present invention, may range, for example, from 0.01% to 10% by weight relative to the total weight of the composition, such as for example, from 0.05% to 5% and further still, from 0.1% to 3% by weight relative to the total weight of the composition.

Amphoteric Polymers

The amphoteric polymers which can be used in the present invention can be chosen, for example, from polymers comprising K and M units distributed statistically in the polymer chain, wherein:

K is a unit derived from a monomer comprising at least one basic nitrogen atom and M is a unit derived from an acid monomer comprising at least one group chosen from carboxylic groups and sulfonic groups; or alternatively K and M, which are identical or different, are each groups chosen from groups derived from zwitterionic monomers of carboxybetaines and groups derived from zwitterionic monomers of sulfobetaines; or alternatively K and M, which are identical or different, may also each be chosen from polymers comprising cationic polymer chains comprising at least one amine group chosen from primary, secondary, tertiary and quaternary amine groups, wherein at least one of the amine groups is substituted with a group chosen from carboxylic groups and sulfonic groups linked via a hydrocarbon group; or alternatively K and M may form part of a chain of a polymer with an α,β-dicarboxylic ethylene unit wherein one of the carboxylic groups has been caused to react with a polyamine comprising at least one amine group chosen from primary amine groups and secondary amine groups.

Representative amphoteric polymers defined above that can be used include the following polymers:

(1) The polymers resulting from the copolymerization of a monomer derived from a vinyl compound substituted with a carboxylic group such as acrylic acid, methacrylic acid, maleic acid, and α-chloroacrylic acid, and of a basic monomer derived from a substituted vinyl compound comprising at least one basic atom such as dialkylaminoalkyl methacrylate and acrylate, dialkylaminoalkyl-methacrylamide and acrylamide. Such compounds are described in U.S. Pat. No. 3,836,537, the disclosure of which related to such compounds is specifically incorporated by reference herein. The sodium acrylate/acrylamidopropyl-trimethylammonium chloride copolymer sold under the name of "POLYQUART KE 3033" by the company HENKEL can also be cited.

The vinyl compound can also be a salt of dialkyldiallylammonium such as diethyldiallylammonium chloride. The copolymers of acrylic acid and the latter monomer are sold under the name "MERQUAT 280", "MERQUAT 295" and "MERQUAT PLUS 3330" by the company CALGON.

(2) The polymers comprising units derived from:
a) at least one monomer chosen from acrylamides substituted on the nitrogen by an alkyl group and methacrylamides substituted on the nitrogen by an alkyl group,
b) at least one acidic comonomer comprising at least one reactive carboxylic group, and
c) at least one basic comonomer such as comonomers chosen from esters of acrylic acid and esters of methacrylic acid, said esters being substituted with at least one amine chosen from primary, secondary, tertiary and quaternary amines, and the product of quaternization of dimethylaminoethyl methacrylate with a sulfate chosen from dimethyl sulfate and diethyl sulfate.

Some embodiments according to the invention utilize N-substituted acrylamides and N-substituted methacrylamides comprising ($C_2$–$C_{12}$)alkyl groups, such as N-ethylacrylamide, N-tert-butylacrylamide, N-tert-octylacrylamide, N-octylacrylamide, N-decylacrylamide, and N-dodecylacrylamide, as well as the corresponding methacrylamides.

The acidic comonomers can be chosen, for example, from acrylic, methacrylic, crotonic, itaconic, maleic and fumaric acids as well as the ($C_1$–$C_4$)alkyl monoesters of entities chosen from maleic anhydride, fumaric anhydride, maleic acid, and fumaric acid.

The basic comonomers can be chosen, for example, from methacrylates of aminoethyl, butylaminoethyl, N,N'-dimethylaminoethyl, and N-tert-butylaminoethyl.

Additionally, the copolymers having the CTFA name (4$^{th}$ edition, 1991) Octylacrylamide/acrylates/butylaminoethylmethacrylate copolymer such as the products sold under the name AMPHOMER and LOVOCRYL 47 by NATIONAL STARCH can also be used.

(3) The partially and completely alkylated and crosslinked polyaminoamides derived from polyaminoamides of formula:

 (X)

wherein:

$R_{19}$ is a divalent group chosen from groups derived from saturated dicarboxylic acids, groups derived from dicarboxylic aromatic acids, groups derived from mono- and dicarboxylic aliphatic acids comprising at least one ethylenic double bond, groups derived from an ester of ($C_1$–$C_6$)alkanols of said acids, and groups derived from the addition of any one of said aforementioned acids with an amine chosen from bis-primary and bis-secondary amines, and Z is a divalent group derived from polyalkylene-polyamines chosen from bis-primary, and mono- and bis-secondary polyalkylene-polyamines, for example, Z represents:

a) in an amount ranging from 60 mol % to 100 mol %, the group

 (XI)

wherein x=2 and p=2 or 3, or alternatively x=3 and p=2, it being understood that group Z of formula a) is derived from a compound chosen from diethylenetriamine, triethylenetetraamine and dipropylenetriamine;

b) in an amount ranging from 0 mol % to 40 mol %, (1) said groups (XI) above in which x=2 and p=1 and which said group is derived from a compound chosen from ethylenediamine, and (2) groups derived from piperazine:

c) in an amount ranging from 0 mol % to 20 mol %, the polyalkylene-polyamine group —NH—(CH$_2$)$_6$—NH—, which is derived from hexamethylenediamine, wherein said polyalkylene-polyamine group is crosslinked by adding a bifunctional crosslinking agent (chosen from the epihalohydrins, diepoxides, dianhydrides, and bis-unsaturated derivatives) present in an amount ranging from 0.025 mol to 0.35 mol of crosslinking agent per amine group of the polyamino amide and alkylated by the action of at least one compound chosen from acrylic acid, chloroacetic acid, alkanesultones, and salts thereof.

The saturated dicarboxylic acids are for example chosen from saturated ($C_6$–$C_{10}$) dicarboxylic acids such as adipic, 2,2,4-trimethyladipic and 2,4,4-trimethyladipic acid.

Representative dicarboxylic aromatic acids include for example ($C_6$–$C_{10}$) dicarboxylic aromatic acids, such as terephthalic acid. And representative mono- and dicarboxylic aliphatic acids comprising at least one ethylenic double bond include for example acrylic, methacrylic and itaconic acids.

The alkanesultones used in the alkylation can, for example, be chosen from propanesultone and butanesultone, and the salts of the alkylating agents can be chosen from sodium and potassium salts of said alkylating agents.

(4) The polymers comprising zwitterionic units of formula:

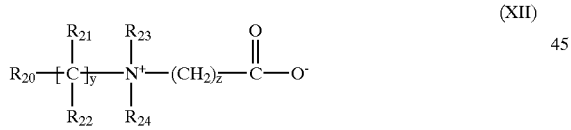

wherein:

$R_{20}$ is chosen from residues of polymerizable unsaturated groups such as acrylate, methacrylate, acrylamide and methacrylamide groups, y and z, which can be identical or different, are each chosen from integers ranging from 1 to 3, $R_{21}$ and $R_{22}$, which may be identical or different, are each chosen from hydrogen, and methyl, ethyl and propyl groups, $R_{23}$ and $R_{24}$, which may be identical or different, are each chosen from hydrogen and alkyl groups, provided that the sum of the carbon atoms in $R_{23}$ and $R_{24}$ does not exceed 10.

The polymers comprising such units may also comprise units derived from nonzwitterionic monomers such as dimethylaminoethyl acrylate, dimethylaminoethyl methacrylate, diethylaminoethyl acrylate, diethylaminoethyl methacrylate, alkyl acrylates, alkyl methacrylates, alkyl acrylamides, alkyl methacrylamides, and vinyl acetate.

By way of example, there may be mentioned the copolymer of methyl methacrylate/methyl dimethylcarboxymethylammonioethyl methacrylate such as the product sold under the name DIAFORMER Z301 by the company SANDOZ.

(5) The polymers derived from chitosan comprising at least one monomeric unit chosen from formulae (XIII), (XIV) and (XV):

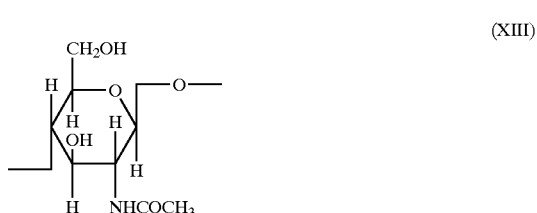

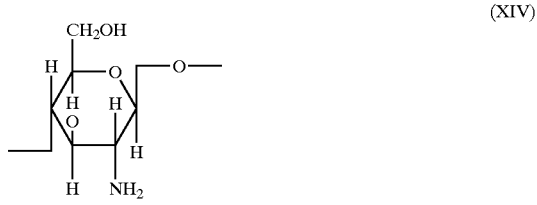

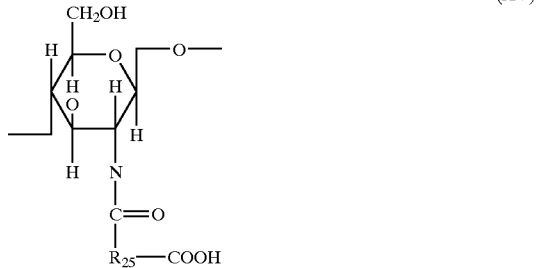

wherein said unit (XIII) is present in an amount ranging for example from 0% to 30%, by weight relative to the total weight of said polymer, said unit (XIV) is present in an amount ranging for example from 5% to 50% by weight relative to the total weight of said polymer, and said unit (XV) is present in an amount ranging for example from 30% to 90% by weight relative to the total weight of said polymer, and wherein in said unit (XV), $R_{25}$ is chosen from groups of formula:

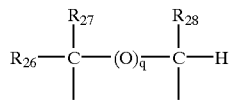

wherein:

q is equal to 0 or 1, and (i) when q is equal to 0, $R_{26}$, $R_{27}$ and $R_{28}$, which may be identical or different, are each chosen from:

hydrogen, methyl, hydroxyl, acetoxy, and amino groups, monoalkylamine and dialkylamine groups optionally interrupted by at least one nitrogen atom and/or optionally substituted with at least one group chosen from amine, hydroxyl, carboxyl, alkylthio and sulfonic groups, and alkylthio groups wherein said alkyl portion of said alkylthio group carries an amino group, provided that at least one of said $R_{26}$, $R_{27}$ and $R_{28}$ groups is chosen from hydrogen; and (ii) when q is equal to 1, $R_{26}$, $R_{27}$ and $R_{28}$, which may be identical or different, are each chosen from hydrogen, and the salts formed by these polymers (5) with bases, and the salts formed by these polymers (5) with acids (6) The polymers derived from the N-carboxyalkylation of chitosan such as N-carboxymethyl chitosan and N-carboxybutyl chitosan sold under the name "EVALSAN" by the company JAN DEKKER.

(7) The polymers of formula (XVI), which are described for example in French Patent 1 400366, the disclosure of which relating to such polymers is specifically incorporated by reference herein:

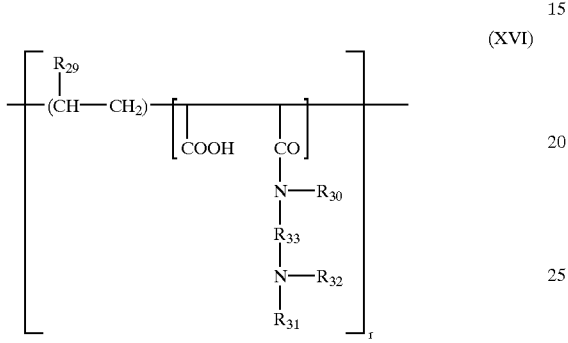

(XVI)

wherein:

r is chosen such that the number-average molecular weight of said polymer ranges from 500 to 6,000,000, such as from 1000 to 1,000,000.

$R_{29}$ is chosen from hydrogen and $CH_3O$, $CH_3CH_2O$, and phenyl groups, $R_{30}$ and $R_{31}$, which are identical or different, are each chosen from hydrogen and lower alkyl groups comprising up to 6 carbon atoms such as methyl and ethyl, $R_{32}$ is chosen from lower alkyl groups comprising up to 6 carbon atoms such as methyl and ethyl and groups of formula: $-R_{33}-N(R_{31})_2$, wherein $R_{31}$ is as defined above and $R_{33}$ is defined below, $R_{33}$ is chosen from $-CH_2-CH_2-$, $-CH_2-CH_2-CH_2-$, and $-CH_2-CH(CH_3)-$.

(8) Amphoteric polymers of the $-D-X-D-X-$ type, which are described for example in U.S. Pat. No. 4,996,059, the disclosure of which relating to amphoteric polymers is specifically incorporated by reference herein, chosen from:

a) polymers derived from reaction of chloroacetic acid or sodium chloroacetate with at least one compound comprising at least one unit of formula (XVII):

(XVII)

wherein D is a group:

and X is chosen from the symbols E and E', wherein E and E', which are identical or different, are each chosen from bivalent groups chosen from alkylene groups comprising at least one chain chosen from linear and branched chains comprising up to 7 carbon atoms in the principal chain, wherein said principal chain is optionally substituted with at least one hydroxyl group, and wherein said alkylene groups optionally comprise at least one atom chosen from oxygen, nitrogen, and sulfur, wherein said at least one optional atom is present in the form of at least one group chosen from ether, thioether, sulfoxide, sulfone, sulfonium, alkylamine and alkenylamine groups, and hydroxyl, benzylamine, amine oxide, quaternary ammonium, amide, imide, alcohol, ester and urethane groups, and wherein said alkylene groups optionally comprise 1 to 3 rings chosen from aromatic rings and heterocyclic rings, b) polymers of formula:

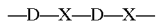

(XIII)

wherein:

D is a group:

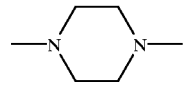

X is chosen from the symbols E and E' and wherein at least one X is chosen from E',-E is chosen from bivalent groups chosen from alkylene groups comprising at least one chain chosen from linear and branched chains comprising up to 7 carbon atoms in the principal chain, wherein said principal chain is optionally substituted with at least one hydroxyl group, and wherein said alkylene groups optionally comprise at least one atom chosen from oxygen, nitrogen, and sulfur, wherein said at least one optional atom is present in the form of at least one group chosen from ether, thioether, sulfoxide, sulfone, sulfonium, alkylamine and alkenylamine groups, and hydroxyl, benzylamine, amine oxide, quaternary ammonium, amide, imide, alcohol, ester and urethane groups, and wherein said alkylene groups optionally comprise 1 to 3 rings chosen from aromatic rings and heterocyclic rings, and E' is a bivalent group chosen from alkylene groups comprising at least one chain chosen from linear and branched chains comprising up to 7 carbon atoms in the principal chain, wherein said principal chain is optionally substituted with at least one hydroxyl group, and wherein said alkylene groups comprise at least one nitrogen atom substituted with an alkyl chain, wherein said alkyl chain is optionally interrupted by an oxygen atom and, wherein said alkyl chain comprises at least one functional group chosen from carboxyl and hydroxyl functional groups, and wherein said at least one alkyl chain is betainized by reaction with a reactant chosen from chloroacetic acid and sodium chloroacetate.

(9) ($C_1-C_5$)alkyl vinyl ether/maleic anhydride copolymers partially modified by semiamidation with an N,N-dialkylaminoalkylamine such as, for example, N,N-dimethylaminopropylamine or by semiesterification with an N,N-dialkanolamine. These copolymers may also comprise other vinyl comonomers such as, for example, vinylcaprolactam.

The amphoteric polymers of family (1), are utilized in certain embodiments of the invention.

According to the invention, the at least one polymer chosen from amphoteric polymers may be present in an amount ranging, for example, from 0.01% to 10% by weight relative to the total weight of the composition, such as from 0.05% to 5% by weight, and further, such as from 0.1% to 3% by weight relative to the total weight of the composition.

The medium, for the composition, which is suitable for dyeing is an aqueous medium comprising water and at least one hydroxylated solvents as described above.

The composition in accordance with the invention may further comprise an effective amount of at least one agent conventionally used in oxidation dyeing, such as at least one adjuvant chosen from, for example, sequestering agents such as EDTA and etidronic acid, UV screening agents, waxes, volatile and non-volatile, cyclic, linear and branched silicones, optionally organomodified with groups such as amine groups, nonionic polymers, anionic polymers, cationic surfactants, anionic surfactants, amphoteric surfactants, nonionic surfactants other than those of already mentioned, amphiphilic polymers comprising at least one fatty chain other than the cationic amphiphilic polymers comprising at least one fatty chain previously mentioned, such as for example, nonionic polymers of polyurethane type, thickeners containing sugar units, preserving agents, ceramides, pseudoceramides, plant oils, mineral oils, synthetic oils, vitamins, provitamins such as for example, panthenol, and opacifiers.

Further non-limiting examples of the at least one agent conventionally used in oxidation dyeing may be chosen from reducing agents and antioxidants, such as for example, sodium sulphite, thioglycolic acid, thiolactic acid, sodium bisulphite, dehydroascorbic acid, hydroquinone, 2-methylhydroquinone, tert-butylhydroquinone and homogentisic acid. The at least one agent may be present in the composition of the invention in an amount ranging from 0.05% to 3% by weight relative to the total weight of the composition, such as for example, from 0.05% to 1.5% by weight relative to the total weight of the composition.

One skilled in the art should take care to select said optionally complementary compounds, such that the advantageous properties intrinsically associated with the dye composition according to the invention are not, or are not substantially, adversely affected by the additions envisaged.

In the composition according to the invention, said at least one composition (B) may comprise at least one oxidizing agent chosen, for example, from hydrogen peroxide, urea peroxide, alkali metal bromates and ferricyanides, and persalts such as perborates and persulfates. For example, hydrogen peroxide may be used. This oxidizing agent advantageously comprises an oxygenated aqueous solution of which the titre may range from 1 to 40 in volume, such as from 5 to 40.

As an oxidizing agent, at least one oxidation-reduction enzyme such as 2-electron oxydoreductases (for example, laccases), peroxydases, and 2-electron oxydoreductases (such as uricase), if necessary in the presence of their corresponding donor or cofactor, may also be used.

The pH of the dyeing composition (A) or of the composition applied to the keratinous fibers [composition resulting from mixing the dye composition (A) and the oxidizing composition (B)], generally ranges from 4 to 12, such as from 6 to 11, and may be adjusted to the desired value by means of at least one agent chosen from acidifying and basifying agents well-known in the art of dyeing keratinous fibers.

Representative basifying agents include aqueous ammonia, alkali metal carbonates, alkanolamines such as for example, those chosen from monoethanolamines, diethanolamines, triethanolamines and derivatives thereof, oxyethylenated hydroxyalkylamines, oxypropylenated hydroxyalkylamines, oxyethylenated ethylenediamines, oxypropylenated ethylenediamines, sodium hydroxide, potassium hydroxide and compounds of formula (XIX):

wherein:
R is a propylene residue optionally substituted with a group chosen from hydroxyl group and $(C_1–C_4)$alkyl groups;

$R_{38}$, $R_{39}$, $R_{40}$ and $R_{41}$, which may be identical or different, are each chosen from hydrogen, $(C_1–C_4)$alkyl groups and hydroxy$(C_1–C_4)$alkyl groups.

Representative acidifying agents include, classically, by way of example, organic and inorganic acids, such as hydrochloric acid, orthophosphoric acid, and carboxylic acids such as, for example, tartaric acid, citric acid, lactic acid, and sulfonic acids.

In one embodiment of the invention, the dyeing process comprises applying on dry or wet keratinous fibers, such as human keratinous fibers like hair, at least one ready-to-use composition, prepared at the time of use from at least one dyeing composition (A) and at least one oxidizing composition (B) and in leaving said at least one ready-to-use composition on said keratinous fibers for a time ranging from 1 to 60 minutes, such as from 10 to 45 minutes, rinsing said keratinous fibers, optionally shampooing said keratinous fibers, rinsing said keratinous fibers after said optional shampooing, and drying said keratinous fibers, wherein said at least one ready-to-use composition comprises:

(1) at least one composition (A) comprising, in a medium suitable for dyeing:
  (a) at least one cationic amphiphilic polymer comprising at least one fatty chain, and
  (b) a combination comprising:
    (I) at least one compound chosen from oxyalkylenated fatty alcohols and glycerolated fatty alcohols, and
    (II) at least one hydroxylated solvent having a molecular weight of less than 250,
  wherein the weight ratio of (I) to (II) is greater than 1:1; and
(2) at least one composition (B) comprising at least one oxidation dye.

Unless otherwise indicated, all numbers expressing quantities of ingredients, properties such as molecular weight, reaction conditions, and so forth used in the specification and claims are to be understood as being modified in all instances by the term "about". Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The following example is intended to illustrate the invention without in anyway limiting the scope thereof.

EXAMPLE

Two oxidation dye compositions were prepared:
one, composition 1, according to the invention, with a weight ratio of oxyethylenated fatty alcohols/hydroxylated solvent (glycerol) equal to 10.8:1,
the other, composition 2, not in accordance with the invention, with a weight ratio of oxyethylenated fatty alcohols/hydroxylated solvent (glycerol) equal to 0.5:1.

| Dye compositions: (expressed in grams %) | | |
|---|---|---|
| Dye compositions | 1 | 2 |
| Oxyethylenated fatty alcohols | 32.5 | 5 |
| Glycerol | 3 | 10 |
| Oleic acid | 2 | 2 |
| Oleyl alcohol | 1.8 | 1.8 |
| Coconut acid monoisopropanolamide | 4 | 4 |
| Cationic amphiphilic polymer: Quatrisoft LM 200 sold by the company Amerchol | 0.3 | 0.3 |
| Non-amphiphilic cationic polymer of formula (W) | 1.8 AM* | 1.8 AM* |
| Amphoteric polymer (Merquat 280 from Calgon) | 1.22 AM* | 1.22 AM* |
| Plant oils | 0.6 | 0.6 |
| Sequestering agent, antioxidant, reducing agent | q.s. | q.s. |
| Aqueous ammonia (20% $NH_3$) | 8 | 8* |
| 1,3-Dihydroxybenzene (resorcinol) | 0.011 | 0.011 |
| Para-phenylenediamine | 0.31 | 0.31 |
| 1-Hydroxy-3-aminobenzene | 0.035 | 0.035 |
| 1-Hydroxy-2-aminobenzene | 0.023 | 0.023 |
| 1-Hydroxy-4-aminobenzene | 0.53 | 0.53 |
| 5-N-(β-hydroxyethyl)amino-2-methylphenol | 1.07 | 1.07 |
| 4-N-methylphenyl sulfate | 0.43 | 0.43 |
| 5-methyl-2-aminophenol | 0.12 | 0.12 |
| Water qs | 100 | 100 |

AM* denotes Active Material

The dye compositions were mixed together, at the time of use, in a plastic bowl, with an oxidizing composition (described below), at a rate of 1 part of dye composition per 1.5 parts of oxidizing composition.

| Oxidizing composition: | |
|---|---|
| Fatty alcohol | 2.3 |
| Oxyethylenated fatty alcohol | 0.6 |
| Fatty amide | 0.9 |
| Glycerol | 0.5 |
| Hydrogen peroxide | 7.5 |
| Fragrance | qs |
| Demineralized water qs | 100 |

Locks of 3 grams of natural hair containing 90% white hairs were each impregnated with the mixtures obtained above (bath ratio: 10 g of mixture per 1 g of hair) and were laid out flat on a support.

The color of these locks was then measured using a Minolta CM2002 colorimeter in the L*a*b* system, at a time T0, T5 minutes and T10 minutes.

In the L*a*b* system, the 3 parameters denote, respectively, the intensity (L*), the shade (a*) and the saturation (b*).

According to this system, the greater the value of L, the lighter or less intense the color. Conversely, the lower the value of L, the darker or more intense the color.

The ΔL relative to the value of L at T0 (LT0) represents a change in the value of L: the more negative the ΔL, the faster the mixture darkens, and thus the greater the oxidation of the mixture.

$$\Delta L5 = LT5 - LT0,$$

$$\Delta L10 = LT10 - LT0.$$

The results are collated in Table (1) below:

TABLE 1

| Colorimetric measurements (average of 5 measurements) | | |
|---|---|---|
| | Composition 1 | Composition 2 |
| LT0 | 25.7 | 25.8 |
| LT5 | 19.0 | 13.0 |
| ΔL5 | −6.7 | −12.8 |
| LT10 | 14.8 | 7.1 |
| ΔL10 | −10.9 | −18.7 |

Conclusion: The ΔL values at 5 and 10 minutes are much more negative in the case of composition 2 not in accordance with the invention than in the case of composition 1 according to the invention, which indicates that the color of the dye mixture changes much less quickly in the case of the invention.

What is claimed:

1. A composition for oxidation dyeing of keratinous fibers comprising, in a medium suitable for dyeing:
   (a) at least one oxidation dye,
   (b) at least one cationic amphiphilic polymer comprising at least one fatty chain, and
   (c) a combination comprising:
      (I) at least one compound chosen from oxyalkylenated fatty alcohols and glycerolated fatty alcohols, and
      (II) at least one hydroxylated solvent having a molecular weight of less than 250,
   wherein the weight ratio of (I) to (II) is greater than 1:1.

2. A composition according to claim 1, wherein said oxyalkylenated fatty alcohols are chosen from formula (IAA):

(IAA)

wherein:
R is chosen from optionally saturated, linear and branched groups containing from 8 to 40 carbon atoms,
Z is chosen from oxyethylenated groups and oxypropylenated groups of formulae (i), (ii)$_1$, and (ii)$_2$:

(i)

(ii)$_1$

(ii)$_2$ and
m is a number ranging from 1 to 250.

3. A composition according to claim 2, wherein m is a number ranging from 2 to 100.

4. A composition according to claim 1, wherein said oxyalkylenated fatty alcohols are chosen from optionally saturated, linear and branched fatty alcohols containing from 10 to 20 carbon atoms and from 2 to 40 ethylene oxide groups.

5. A composition according to claim 1, wherein said glycerolated fatty alcohols are chosen from formula (IBB):

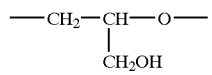

wherein:
R is chosen from optionally saturated, linear and branched groups containing from 8 to 40 carbon atoms,
Z is chosen from glycerolated groups of formula (iii):

$$-CH_2-CH-O-$$
$$\hspace{1.5em}|$$
$$\hspace{1em}CH_2OH$$

(iii)

and
n is a number ranging from 1 to 30.

6. A composition according to claim 5, wherein n is a number ranging from 1 to 10.

7. A composition according to claim 1, wherein said at least one compound chosen from oxyalkylenated fatty alcohols and glycerolated fatty alcohols is present in an amount ranging from 0.05% to 50% by weight relative to the total weight of the composition.

8. A composition according to claim 7, wherein said at least one compound chosen from oxyalkylenated fatty alcohols and glycerolated fatty alcohols is present in an amount ranging from 2% to 40% by weight relative to the total weight of the composition.

9. A composition according to claim 1, wherein said at least one hydroxylated solvent comprises from 2 to 12 carbon atoms.

10. A composition according to claim 9, wherein said at least one hydroxylated solvent comprises from 2 to 8 carbon atoms.

11. A composition according to claim 10, wherein said at least one hydroxylated solvent comprises from 2 to 3 carbon atoms.

12. A composition according to claim 1, wherein said at least one hydroxylated solvent is chosen from ethyl alcohol, propyl alcohol, n-butyl alcohol, polyol ethers and ($C_2$–$C_6$) polyols.

13. A composition according to claim 12, wherein said ($C_2$–$C_6$)polyols are chosen from 2-methyl-1,3-butanediol, 2,2-dimethyl-1,3-propanediol, 2-methyl-1,3-propanediol, 2-methyl-2,4-pentanediol, 1,5-pentanediol, and 3-methyl-1,5-pentanediol.

14. A composition according to claim 12, wherein said ($C_2$–$C_6$)polyols are chosen from glycerol, propylene glycol, dipropylene glycol and 1,3-propanediol.

15. A composition according to claim 12, wherein said at least one hydroxylated solvent is chosen from polyol ethers comprising at least one free hydroxyl function.

16. A composition according to claim 15, wherein said polyol ethers are chosen from ($C_1$–$C_8$)ethers of ($C_2$–$C_9$) glycols.

17. A composition according to claim 16, wherein said polyol ethers are chosen from ethylene glycol monobutyl ether, ethylene glycol monophenyl ether, ethylene glycol monobenzyl ether, propylene glycol monomethyl ether, propylene glycol monoethyl ether, diethylene glycol monomethyl ether, diethylene glycol monoethyl ether, dipropylene glycol monomethyl ether, tripropylene glycol monomethyl ether, propylene glycol monophenyl ether, propylene glycol monobenzyl ether, diethylene glycol monophenyl ether, and diethylene glycol monobenzyl ether.

18. A composition according to claim 1, wherein said at least one hydroxylated solvent is present in said composition in an amount ranging from 0.01% to 25% by weight relative to the total weight of the composition.

19. A composition according to claim 18, wherein said at least one hydroxylated solvent is present in said composition in an amount ranging from 0.1% to 20% by weight relative to the total weight of the composition.

20. A composition according to claim 1, wherein the at least one hydroxylated solvent is chosen from linear and branched compounds bearing at least one —OH function.

21. A composition according to claim 1, wherein the weight ratio of said at least one compound chosen from oxyalkylenated fatty alcohols and glycerolated fatty alcohols, and said at least one hydroxylated solvent ranges from greater than 1:1 to 30:1.

22. A composition according to claim 21, wherein the weight ratio of said at least one compound chosen from oxyalkylenated fatty alcohols and glycerolated fatty alcohols, and said at least one hydroxylated solvent ranges from 1.5:1 to 20:1.

23. A composition according to claim 1, wherein said at least one oxidation dye is chosen from oxidation bases and oxidation couplers.

24. A composition according to claim 23, wherein said oxidation bases are chosen from ortho-phenylenediamines, para-phenylenediamines, double bases, ortho-para-aminophenols, para-aminophenols, heterocyclic bases, and their acid addition salts.

25. A composition according to claim 24, wherein said para-phenylenediamines are chosen from compounds of formula (I), and their acid addition salts:

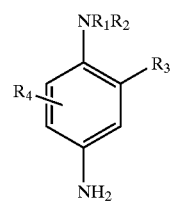

(I)

wherein:
R$_1$ is chosen from hydrogen, $C_1$–$C_4$ alkyl groups, monohydroxy($C_1$–$C_4$ alkyl) groups, polyhydroxy ($C_2$–$C_4$ alkyl) groups, ($C_1$–$C_4$)alkoxy($C_1$–$C_4$)alkyl groups, phenyl groups, 4'-aminophenyl groups, and $C_1$–$C_4$ alkyl groups substituted with at least one group chosen from nitrogen-containing groups, R$_2$ is chosen from hydrogen, $C_1$–$C_4$ alkyl groups, monohydroxy($C_1$–$C_4$ alkyl) groups, polyhydroxy ($C_2$–$C_4$ alkyl) groups, ($C_1$–$C_4$)alkoxy($C_1$–$C_4$)alkyl groups, and $C_1$–$C_4$ alkyl groups substituted with a substituent chosen from nitrogen-containing groups;

R$_1$ and R$_2$ may also form, together with the nitrogen to which they are bonded, a 5- or 6-membered nitrogen-containing heterocycle ring, optionally substituted with at least one group chosen from alkyl groups, hydroxyl groups and ureido groups;

R$_3$ is chosen from hydrogen, halogens, $C_1$–$C_4$ alkyl groups, sulfo groups, carboxyl groups, monohydroxy($C_1$–$C_4$ alkyl) groups, hydroxy($C_1$–$C_4$ alkyoxy) groups, acetylamino($C_1$–$C_4$ alkoxy)

groups, mesylamino($C_1$–$C_4$ alkoxy) groups, and carbamoylamino($C_1$–$C_4$ alkoxy) groups;

$R_4$ is chosen from hydrogen, halogens, and $C_1$–$C_4$ alkyl groups.

26. A composition according to claim 24, wherein said para-phenylenediamines are chosen from para-phenylenediamine, para-toluylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-amino-N,N-bis(β-hydroxyethyl)-3-methylaniline, 4-amino-3-chloro-N,N-bis(β-hydroxyethyl)aniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine and 2-β-hydroxyethyloxy-para-phenylenediamine, and their acid addition salts.

27. A composition according to claim 25, wherein said nitrogen-containing groups are chosen from amino, mono($C_1$–$C_4$)alkylamino, di($C_1$–$C_4$)alkylamino, tri($C_1$–$C_4$) alkylamino, monohydroxy($C_1$–$C_4$)alkylamino, imidazolinium groups and ammonium groups.

28. A composition according to claim 24, wherein said double bases are chosen from the compounds of formula (II) and their acid addition salts:

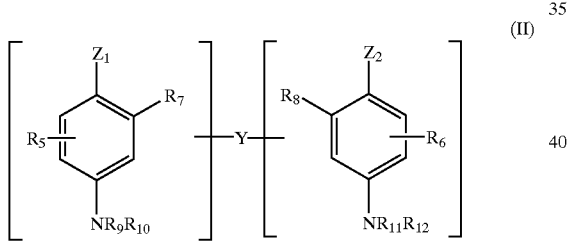

(II)

wherein:

$Z_1$ and $Z_2$, which may be identical or different, are each chosen from hydroxyl groups, and —$NH_2$ groups, optionally substituted with a group chosen from $C_1$–$C_4$ alkyl groups, and linkers Y linker Y is chosen from linear and branched, divalent alkylene groups comprising from 1 to 14 carbon atoms, optionally interrupted by, or optionally terminating with, at least one entity chosen from nitrogen-containing groups and heteroatoms, and optionally substituted with at least one group chosen from hydroxyl groups, and $C_1$–$C_6$ alkoxy groups;

$R_5$ and $R_6$, which may be identical or different, are each chosen from hydrogen, halogens, $C_1$–$C_4$ alkyl groups, monohydroxy($C_1$–$C_4$ alkyl) groups, polyhydroxy($C_2$–$C_4$ alkyl) groups, amino($C_1$–$C_4$ alkyl) groups, and linkers Y;

$R_7$, $R_8$, $R_9$, $R_{10}$, $R_{11}$ and $R_{12}$, which may be identical or different, are each chosen from hydrogen, linkers Y, and $C_1$–$C_4$ alkyl groups;

provided that said compounds of formula (II) comprise only one linker Y per molecule.

29. A composition according to claim 28, wherein said nitrogen-containing groups are chosen from amino, mono($C_1$–$C_4$)alkylamino, di($C_1$–$C_4$)alkylamino, tri($C_1$–$C_4$) alkylamino, monohydroxy($C_1$–$C_4$)alkylamino, imidazolinium groups and ammonium groups.

30. A composition according to claim 24, wherein said double bases are chosen from N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine, 1,8-bis(2,5-diaminophenoxy)-3,5-dioxaoctane, and their acid addition salts.

31. A composition according to claim 24, wherein said para-aminophenols are chosen from compounds of formula (III), and their acid addition salts:

(III)

wherein:

$R_{13}$ is chosen from hydrogen, halogens, $C_1$–$C_4$ alkyl groups, monohydroxy($C_1$–$C_4$ alkyl) groups, ($C_1$–$C_4$) alkoxy($C_1$–$C_4$)alkyl groups, amino($C_1$–$C_4$ alkyl), and hydroxy($C_1$–$C_4$)alkylamino($C_1$–$C_4$ alkyl) groups;

$R_{14}$ is chosen from hydrogen, halogens, $C_1$–$C_4$ alkyl groups, monohydroxy($C_1$–$C_4$ alkyl) groups, polyhydroxy($C_2$–$C_4$ alkyl) groups, amino($C_1$–$C_4$ alkyl) groups, cyano($C_1$–$C_4$ alkyl) groups, and ($C_1$–$C_4$)alkoxy($C_1$–$C_4$)alkyl groups.

32. A composition according to claim 24, wherein said para-aminophenols are chosen from para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(-hydroxyethylaminomethyl)phenol, and their acid addition salts.

33. A composition according to claim 24, wherein said heterocyclic bases are chosen from pyridine derivatives, pyrimidine derivatives, and pyrazole derivatives.

34. A composition according to claim 24, wherein said ortho-aminophenols are chosen from from 2-aminophenol, 2-amino-1-hydroxy-5-methylbenzene, 2-amino-6-methylbenzene, 5-acetamido-2-aminophenol, and their acid addition salts.

35. A composition according to claim 24, wherein said oxidation bases are present in an amount ranging from 0.0005% to 12% by weight relative to the total weight of the composition.

36. A composition according to claim 35, wherein said oxidation bases are present in an amount ranging from 0.005% to 8% by weight relative to the total weight of the composition.

37. A composition according to claim 23, wherein said oxidation couplers are chosen from meta-phenylenediamines, meta-aminophenols, meta-diphenols, naphthols, sesamol and its derivatives, heterocyclic couplers, and their acid addition salts.

38. A composition according to claim 23, wherein said oxidation couplers are present in amounts ranging from 0.0001% to 10% by weight relative to the total weight of the composition.

39. A composition according to claim 38, wherein said oxidation couplers are present in amounts ranging from 0.005% to 5% by weight relative to the total weight of the composition.

40. A composition according to claim 24, wherein said acid addition salts are chosen from hydrochlorides, hydrobromides, sulfates, tartrates, lactates and acetates.

41. A composition according to claim 1, wherein said at least one cationic amphiphilic polymer comprising at least one fatty chain is chosen from:
   (i) quaternized celluloses modified with at least one group comprising at least one fatty chain, wherein said at least one group is chosen from alkyl groups, arylalkyl groups, and alkylaryl groups and contains at least 8 carbon atoms;
   (ii) quaternized hydroxyethylcelluloses modified with at least one group comprising at least one fatty chain, wherein said at least one group is chosen from alkyl groups, arylalkyl groups, and alkylaryl groups and contains at least 8 carbon atoms;
   (iii) cationic amphiphilic polyurethanes with at least one hydrophobic group comprising from 10 to 30 carbon atoms,
   (iv) cationic amphiphilic polyvinyllactams, and
   (v) an acrylic terpolymer formed from ($C_{10}$–$C_{30}$)alkyl acrylates, amino(meth)acrylates and itaconate polyoxyethylenated with 20 mol of ethylene oxide.

42. A composition according to claim 41, wherein the alkyl groups of said quaternized celluloses and quaternized hydroxyethylcelluloses comprise from 8 to 30 carbon atoms.

43. A composition according to claim 41, wherein the alkyl groups of said quaternized hydroxyethylcelluloses are chosen from $C_{12}$ alkyl groups and $C_{18}$ alkyl groups.

44. A composition according to claim 1, wherein said at least one cationic amphiphilic polyurethane is chosen from polymers of formula (Ia):

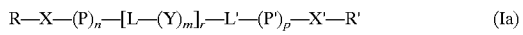

$$R—X—(P)_n—[L—(Y)_m]_r—L'—(P')_p—X'—R' \quad (Ia)$$

wherein:
   R and R', which may be identical or different, are each chosen from hydrophobic groups and hydrogen atoms;
   X and X', which may be identical or different, represent a group comprising an amine function optionally comprising a hydrophobic group, and a group L";
   L, L", and L' which may be identical or different, are each chosen from derivatives of diisocyanates;
   P and P', which may be identical or different, are each chosen from groups comprising an amine function optionally bearing at least one hydrophobic group;
   Y is chosen from hydrophilic groups;
   r is an integer from 1 to 100;
   n, m and p which may be identical or different, are chosen from numbers ranging from 0 to 1000;
   provided that said cationic amphiphilic polyurethanes comprise at least one group chosen from protonated amine functions, and quaternized amine functions, and at least one group chosen from hydrophobic groups.

45. A composition according to claim 1, wherein said at least one cationic amphiphilic polymer comprising at least one fatty chain is present in an amount ranging from 0.01% to 3% by weight relative to the total weight of the composition.

46. A composition according to claim 45, wherein said at least one cationic amphiphilic polymer comprising at least one fatty chain is present in an amount ranging from 0.02% to 0.5% by weight relative to the total weight of the composition.

47. A composition according to claim 1, further comprising at least one direct dye.

48. A composition according to claim 47, wherein said at least one direct dye is present in an amount ranging from 0.001% to 20% by weight relative to the total weight of the composition.

49. A composition according to claim 1, further comprising at least one agent chosen from reducing agents and antioxidants.

50. A composition according to claim 49, wherein said at least one agent is present in the composition of the invention in an amount ranging from 0.05% to 3% by weight relative to the total weight of the composition.

51. A composition according to claim 1, further comprising at least one adjuvant chosen from sequestering agents, UV screening agents, waxes, volatile and non-volatile, cyclic, linear and branched silicones, optionally organomodified with amine groups, nonionic polymers, anionic polymers, cationic surfactants, anionic surfactants, and amphoteric surfactants, nonionic surfactants other than said oxyalkylenated fatty alcohols and said glycerolated fatty alcohols, amphiphilic polymers containing a fatty chain other than said at least one cationic amphiphilic polymers with a fatty chain, thickeners containing sugar units, preserving agents, ceramides, pseudoceramides, plant oils, mineral oils, synthetic oils, vitamins, provitamins, and opacifiers.

52. A ready-to-use composition for the oxidation dyeing of keratinous fibers comprising, in a medium suitable for dyeing:
   (a) at least one oxidation dye,
   (b) at least one cationic amphiphilic polymer comprising at least one fatty chain, and
   (c) a combination comprising:
      (I) at least one compound chosen from oxyalkylenated fatty alcohols and glycerolated fatty alcohols, and
      (II) at least one hydroxylated solvent having a molecular weight of less than 250,
         wherein the weight ratio of (I) to (II) is greater than 1:1; and
   (d) at least one oxidizing agent.

53. A ready-to-use composition according to claim 52, wherein said at least one oxidizing agent is chosen from hydrogen peroxide, urea peroxide, alkali metal bromates, alkali metal ferricyanides, persalts, and oxidation-reduction enzymes, wherein said oxidation-reduction enzymes may be in the presence of their corresponding donor or cofactor.

54. A ready-to-use composition according to claim 53, wherein said at least one oxidizing agent is hydrogen peroxide.

55. A ready-to-use composition according to claim 54, wherein said at least one oxidizing agent is an aqueous hydrogen peroxide solution with a titre ranging from 1 to 40 volumes.

56. A composition according to claim 1, wherein said composition has a pH ranging from 4 to 12.

57. A ready-to-use composition according to claim 52, wherein said composition has a pH ranging from 4 to 12.

58. A ready-to-use composition according to claim 52, further comprising at least one polymer chosen from amphoteric polymers and cationic polymers other than said at least one cationic amphiphilic polymer comprising at least one fatty chain.

59. A ready-to-use composition according to claim 58, wherein said cationic polymers are chosen from poly (quaternary ammonium) polymers comprising repeating units of formula (W):

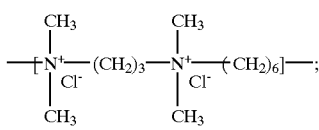

(W)

60. A ready-to-use composition according to claim 58, wherein said cationic polymers are chosen from poly (quaternary ammonium) polymers comprising repeating units of formula (U):

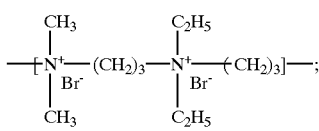

(U)

61. A ready-to-use composition according to claim 58, wherein said amphoteric polymers are copolymers comprising at least one acrylic acid monomer and a dimethyldiallylammonium salt.

62. A ready-to-use composition according to claim 58, wherein said at least one polymer is present in an amount ranging from 0.01% to 10% by weight relative to the total weight of the composition.

63. A ready-to-use composition according to claim 62, wherein said at least one polymer is present in an amount ranging from 0.05% to 5% by weight relative to the total weight of the composition.

64. A ready-to-use composition according to claim 63, wherein said at least one polymer is present in an amount ranging from 0.1% to 3% by weight relative to the total weight of the composition.

65. A process for dyeing keratinous fibers comprising:
(1) storing a composition (A) comprising, in a medium suitable for dyeing:
(a) at least one oxidation dye,
(b) at least one cationic amphiphilic polymer comprising at least one fatty chain, and
(c) a combination comprising:
(I) at least one compound chosen from oxyalkylenated fatty alcohols and glycerolated fatty alcohols, and
(II) at least one hydroxylated solvent having a molecular weight of less than 250,
wherein the weight ratio of (I) to (II) is greater than 1:1;
(2) storing, separately from said composition (A), a composition (B) comprising, in a medium suitable for dyeing, at least one oxidizing agent;
(3) applying said composition (A) and said composition (B) to keratinous fibers, and
(4) developing a color on keratinous fibers;
wherein said composition (A) is combined at the time of use with said composition (B) and applied to the keratinous fibers, or wherein said composition (A) and said composition (B) are applied sequentially to said at least one dyeing composition without intermediate rinsing.

66. A device or kit for the oxidation dyeing of keratinous fibers, comprising at least two compartments, wherein:
(1) a first compartment comprises, in a medium suitable for dyeing:
(a) at least one oxidation dye,
(b) at least one cationic amphiphilic polymer comprising at least one fatty chain, and
(c) a combination comprising:
(I) at least one compound chosen from oxyalkylenated fatty alcohols and glycerolated fatty alcohols, and
(II) at least one hydroxylated solvent having a molecular weight of less than 250,
wherein the weight ratio of (I) to (II) is greater than 1:1; and
(2) a second compartment comprising, in a medium suitable for dyeing, at least one oxidizing agent.

67. A composition for oxidation dyeing of keratinous fibers comprising, in a medium suitable for dyeing:
(a) at least one oxidation dye,
(b) at least one cationic amphiphilic polymer comprising at least one fatty chain, and
(c) a combination comprising:
(I) at least one compound chosen from oxyalkylenated fatty alcohols and glycerolated fatty alcohols, and
(II) at least one hydroxylated solvent,
wherein the weight ratio of (I) to (II) is greater than 1:1.

68. A composition according to claim 1, wherein said oxyalkylenated fatty alcohols are chosen from linear and branched, saturated and unsaturated oxyalkylenated fatty alcohols comprising from 8 to 40 carbon atoms and from 1 to 250 groups chosen from ethylene oxide and propylene oxide groups.

69. A composition according to claim 2 wherein R is chosen from optionally saturated, linear and branched groups containing from 8 to 30 carbon atoms.

70. A composition according to claim 5 wherein R is chosen from optionally saturated, linear and branched groups containing from 8 to 30 carbon atoms.

71. A composition according to claim 1, wherein said glycerolated fatty alcohols are chosen from linear and branched, saturated and unsaturated glycerolated fatty alcohols comprising from 8 to 40 carbon atoms and from 1 to 30 glycerol groups.

72. A composition according to claim 1, wherein said at least one oxidation dye comprises at least one oxidation base and at least one coupler.

73. A composition according to claim 72, wherein said at least one oxidation base is chosen from ortho-phenylenediamines, para-phenylenediamines, double bases, ortho-para-aminophenols, para-aminophenols, heterocyclic bases, and their acid addition salts.

74. A composition according to claim 25 wherein for $R_3$ and $R_4$, said halogens are chosen from chlorine and fluorine.

75. A composition according to claim 28, wherein for linker Y, said heteroatoms are chosen from oxygen, sulfur, and nitrogen.

76. A composition according to claim 31, wherein for $R_{13}$ and $R_{14}$, said halogens are chosen from fluorine.

77. A composition according to claim 37, wherein said naphthols are chosen from monohydroxylated naphthalene derivatives and polyhydroxylated naphthalene derivatives.

78. A composition according to claim 44, wherein r is an integer from 1 to 50.

79. A composition according to claim 44, wherein r is an integer from 1 to 25.

80. A process according to claim 65, wherein said keratinous fibers are hair.

81. A process according to claim 80, wherein said hair is human hair.

82. A composition according to claim 1, wherein said at least one cationic amphiphilic polymer comprising at least one fatty chain is chosen from the cationic amphiphilic polyurethanes of formula (Ia):

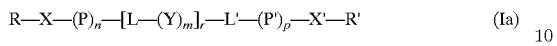

(Ia)

wherein:
R and R' which may be identical or different, are each chosen from hydrophobic groups,
X and X' which may be identical or different, are each chosen from a group L";
n and p which may be identical or different, are each chosen from numbers ranging from 1 to 1000;
L, L", and L' which may be identical or different, are each chosen from derivatives of diisocyanates;
P and P', which may be identical or different, are each chosen from groups comprising an amine function optionally comprising at least one hydrophobic group;
Y is chosen from hydrophilic groups;
r is an integer from 1 to 100;
and m is a number ranging from 0 to 1000.

83. A composition according to claim 1, wherein said at least one cationic amphiphilic polymer comprising at least one fatty chain is chosen from the cationic amphiphilic polyurethanes of formula (Ia):

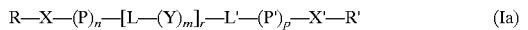

(Ia)

wherein:
R and R' which may be identical or different, are each chosen from hydrophobic groups,
X and X' which may be identical or different, are each chosen from a group L",
n and p are each equal to zero;
L, L", and L' which may be identical or different, are each chosen from derivatives of diisocyanates;
P and P', which may be identical or different, are each chosen from groups comprising an amine function optionally bearing at least one hydrophobic group;
Y is chosen from hydrophilic groups;
r is an integer from 1 to 100;
and m is a number ranging from 0 to 1000.

84. A composition according to claim 1, wherein said at least one cationic amphilic polymer comprising at least one fatty chain is chosen from the cationic amphiphilic polyurethanes of formula (Ia):

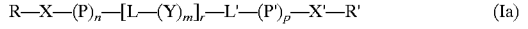

(Ia)

wherein:
R and R' which may be identical or different, are each chosen from hydrophobic groups,
X and X' which may be identical or different, are each chosen from groups comprising a quaternary amine,
n and p are each equal to 0,
L, L", and L' which may be identical or different, are each chosen from derivatives of diisocyanates;
P and P', which may be identical or different, are each chosen from groups comprising an amine function optionally bearing at least one hydrophobic group;
Y is chosen from hydrophilic groups;
r is an integer from 1 to 100; and m is a number ranging from 0 to 1000.

85. A composition according to claim 44, wherein said hydrophobic groups are chosen from hydrocarbon-based groups comprising at least 10 carbon atoms.

86. A composition according to claim 44, wherein X and X' are chosen from amines of following formulae:

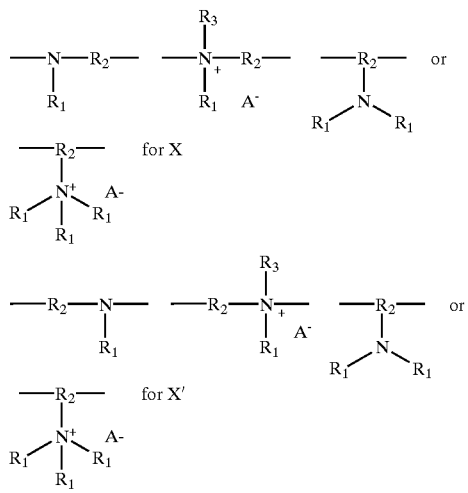

wherein:
$R_2$ which may be identical or different, are each chosen from linear and branched, alkylene groups containing from 1 to 20 carbon atoms, wherein said linear and branched alkylene groups optionally comprise a unit chosen from saturated rings and unsaturated rings, and further wherein at least one carbon atom is optionally replaced with a hetero atom chosen from N, S, O and P;
$R_1$ and $R_3$, which may be identical or different, are each chosen from linear and branched $(C_1-C_{30})$alkyl groups, linear and branched $(C_1-C_{30})$alkenyl groups, and an aryl group, wherein at least one carbon atom is optionally replaced with a hetero atom chosen from N, S, O and P; and
A– which may be identical or different, are each chosen from physiologically acceptable counterions.

87. A composition according to claim 44, wherein the groups L, L', and L" represent a group of formula:

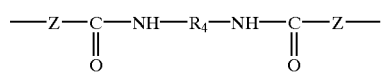

wherein:
Z is a group chosen from —O—, —S—, and —NH—; and
$R_4$ is chosen from linear and branched, alkylene groups containing from 1 to 20 carbon atoms, wherein said linear and branched alkylene groups optionally comprise a unit chosen from saturated rings and unsaturated rings, and further wherein at least one carbon atom is optionally replaced with a hetero atom chosen from N, S, O and P.

88. A composition according to claim 44, wherein P and P', which may be identical or different, are each chosen from groups of the following formulae:

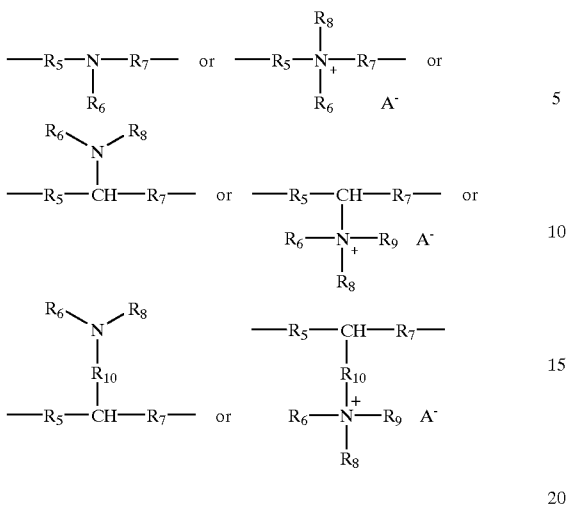

wherein:

$R_5$ and $R_7$, which may be identical or different, are each chosen from linear and branched, alkylene groups containing from 1 to 20 carbon atoms, wherein said linear and branched alkylene groups optionally comprise a unit chosen from saturated rings and unsaturated rings, and further wherein at least one carbon atom is optionally replaced with a hetero atom chosen from N, S, O and P;

$R_6$, $R_8$ and $R_9$, which may be identical or different, are each chosen from linear and branched $(C_1-C_{30})$alkyl groups, linear and branched $(C_1-C_{30})$alkenyl and an aryl group, wherein at least one carbon atom is optionally replaced with a hetero atom chosen from N, S, O and P;

$R_{10}$, which may be identical or different, are each chosen from optionally unsaturated, linear and branched, alkylene groups, optionally comprising at least one hetero atom chosen from N, O, S and P, and A– which may be identical or different, are each chosen from physiologically acceptable counterions.

89. A composition according to claim 1, wherein said at least one cationic amphiphilic polymer comprising at least one fatty chain is chosen from cationic poly(vinyllactam) polymers formed from at least one monomer chosen from:

a) vinyllactam monomers and alkylvinyllactam monomers;

b) monomers chosen from formulae (Ib) and (IIb):

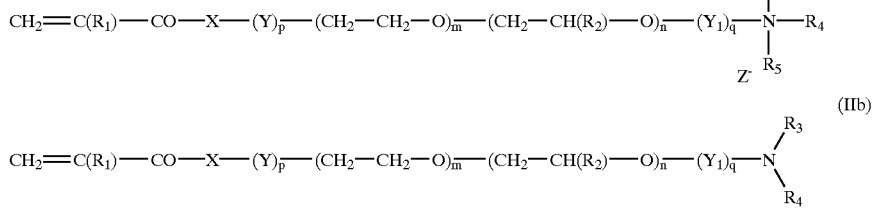

wherein:

X which may be identical or different, are each chosen from oxygen and $NR_6$ groups, $R_1$ and $R_6$ which may be identical or different, are each chosen from hydrogen and linear and branched $(C_1-C_5)$alkyl groups, $R_2$ which may be identical or different, are each chosen from linear and branched $(C_1-C_4)$alkyl groups, $R_3$, $R_4$, and $R_5$ which may be identical or different, are each chosen from hydrogen, linear and branched $(C_1-C_{30})$alkyl groups and groups chosen from formula (IIIb):

$$—(Y_2)_r—(CH_2—CH(R_7)—O)_x—R_8 \qquad (IIIb)$$

wherein:

Y, $Y_1$, and $Y_2$ which are identical or different, are each chosen from linear and branched $(C_2-C_{16})$ alkylene groups, $R_7$ is chosen from hydrogen, linear and branched $(C_1-C_4)$alkyl groups, and linear and branched $(C_1-C_4)$hydroxyalkyl groups, $R_8$ is chosen from hydrogen and linear and branched $(C_1-C_{30})$alkyl groups, p, q, and r which are identical or different, are each a number chosen from 0 and 1, m and n which are identical or different, are each an integer ranging from 0 to 100, x is an integer ranging from 1 to 100, Z is an anion chosen from organic acid anions and inorganic acid anions, provided that:

at least one of $R_3$, $R_4$, $R_5$, and $R_8$ is chosen from linear and branched $(C_9-C_{30})$alkyl groups, if at least one of m and n is other than zero, then q is equal to 1, if at least one of m and n are equal to zero, then at least one of p and q is equal to 0.

90. A composition according to claim 1, wherein said at least one cationic amphiphilic polymer comprising at least one fatty chain is chosen from acrylic terpolymers formed from:

(a) an acrylate monomer (a) chosen from $(C_1-C_6)$alkyl acrylates and $(C_1-C_6)$alkyl methacrylates, wherein said acrylate monomer (a) ranges from 5% to 80% by weight;

(b) a monomer (b) chosen from heterocyclic vinyl compounds containing at least one atom chosen from nitrogen and sulfur, (meth)acrylamides, mono$(C_1-C_4)$ alkylamino$(C_1-C_4)$alkyl (meth)acrylates, di$(C_1-C_4)$ alkylamino$(C_1-C_4)$alkyl (meth)acrylates, mono $(C_1-C_4)$alkylamino$(C_1-C_4)$alkyl(meth)acrylamides and di$(C_1-C_4)$alkylamino$(C_1-C_4)$alkyl(meth) acrylamides, wherein said monomer (b) ranges from 5% to 80% by weight;

a monomer (c) chosen from:

(i) a urethane formed from a monoethylenic unsaturated isocyanate and a nonionic surfactant with a ($C_{1-6}$)alkoxy end, (ii) a block copolymer formed from 1,2-butylene oxide and of 1,2-ethylene oxide, (iii) a copolymerizable ethylenic unsaturated surfactant monomer obtained by condensation of a nonionic surfactant with an α,β-ethylenic unsaturated carboxylic acid or its anhydride, (iv) a surfactant monomer (iv) chosen from the products formed from a monoethylenic unsaturated monoisocyanate with a nonionic surfactant containing an amine function, (v) a monomer chosen from (meth)allyl ethers of formula $CH_2=CR_1CH_2OA_mB_nA_pR_2$, wherein $R_1$ is chosen from a hydrogen atom and a methyl group, A is chosen from a propylenoxy group and a butylenoxy group, B is an ethylenoxy group, n is chosen from zero and integers less than or equal to 200, m and p, which are identical or different are each chosen from zero and integers less than n, and $R_2$ is a hydrophobic group of at least 8 carbon atoms, and (vi) a nonionic monomer of urethane type formed from a monohydric nonionic surfactant with a monoethylenic unsaturated isocyanate, wherein said monomer (c) ranges from 0.1% to 30% by weight; further wherein the weight percentages of said above defined monomers are based on the total weight of said monomers forming the acrylic terpolymer.

91. A composition according to claim 37, wherein said acid addition salts are chosen from hydrochlorides, hydrobromides, sulfates, tartrates, lactates and acetates.

92. A composition according to claim 1, further comprising at least one polymer chosen from amphoteric polymers and cationic polymers other than said at least one cationic amphiphilic polymer comprising at least one fatty chain.

93. A composition according to claim 92, wherein said cationic polymers are chosen from poly(quaternary ammonium) polymers comprising repeating units of formula (W):

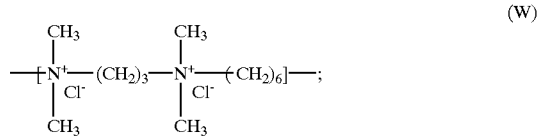

94. A composition according to claim 92, wherein said cationic polymers are chosen from poly(quaternary ammonium) polymers comprising repeating units of formula (U):

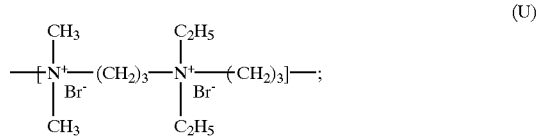

95. A composition according to claim 92, wherein said amphoteric polymers are copolymers comprising at least one acrylic acid monomer and a dimethyldiallylammonium salt.

96. A composition according to claim 92, wherein said at least one polymer is present in an amount ranging from 0.01% to 10% by weight relative to the total weight of the composition.

97. A composition according to claim 96, wherein said at least one polymer is present in an amount ranging from 0.05% to 5% by weight relative to the total weight of the composition.

98. A composition according to claim 97, wherein said at least one polymer is present in an amount ranging from 0.1% to 3% by weight relative to the total weight of the composition.

* * * * *

UNITED STATES PATENT AND TRADEMARK OFFICE
CERTIFICATE OF CORRECTION

PATENT NO. : 6,602,303 B2  Page 1 of 1
DATED : August 5, 2003
INVENTOR(S) : Laurent et al.

It is certified that error appears in the above-identified patent and that said Letters Patent is hereby corrected as shown below:

Column 40,
Line 67, "alkyoxy)" should read -- alkoxy) --.

Column 42,
Line 53, "from from" should read -- from --.

Column 45,
After the formula (W), ";" should read -- . --.
After the formula (U), ";" should read -- . --.

Column 47,
Line 49, "amphilic" should read -- amphiphilic --.

Column 52,
After the formula (W), ";" should read -- . --.
After the formula (U), ";" should read -- . --.

Signed and Sealed this

Fourth Day of November, 2003

JAMES E. ROGAN
*Director of the United States Patent and Trademark Office*